(12) United States Patent
Keser et al.

(10) Patent No.: US 10,729,708 B2
(45) Date of Patent: Aug. 4, 2020

(54) STABILIZED GLYCOPEPTIDE ANTIBIOTIC FORMULATIONS

(71) Applicant: XELLIA PHARMACEUTICALS APS, Kobenhavn S (DK)

(72) Inventors: Sabina Keser, Zagreb (HR); Ivona Jasprica, Zagreb (HR); Jerome LeCunff, Bribir (HR)

(73) Assignee: Xellia Pharmaceuticals APS (DK)

( * ) Notice: Subject to any disclaimer, the term of this patent is extended or adjusted under 35 U.S.C. 154(b) by 0 days.

(21) Appl. No.: 16/300,137

(22) PCT Filed: May 4, 2017

(86) PCT No.: PCT/EP2017/060653
§ 371 (c)(1),
(2) Date: Nov. 9, 2018

(87) PCT Pub. No.: WO2017/194385
PCT Pub. Date: Nov. 16, 2017

(65) Prior Publication Data
US 2019/0175632 A1    Jun. 13, 2019

Related U.S. Application Data

(60) Provisional application No. 62/333,357, filed on May 9, 2016.

(51) Int. Cl.
| A61K 38/14 | (2006.01) |
| A61K 31/704 | (2006.01) |
| A61K 9/00 | (2006.01) |
| A61K 47/18 | (2017.01) |
| A61K 9/08 | (2006.01) |
| A61K 47/40 | (2006.01) |

(52) U.S. Cl.
CPC .......... *A61K 31/704* (2013.01); *A61K 9/0019* (2013.01); *A61K 9/08* (2013.01); *A61K 38/14* (2013.01); *A61K 47/183* (2013.01); *A61K 47/40* (2013.01)

(58) Field of Classification Search
CPC .......... A61K 38/14; A61K 47/40; C07K 9/008
See application file for complete search history.

(56) References Cited

U.S. PATENT DOCUMENTS

| 4,670,258 | A | 6/1987 | Harris et al. | |
| 4,885,275 | A | 12/1989 | Robison | |
| 7,635,773 | B2 * | 12/2009 | Antle | A61K 31/724 |
| | | | | 536/120 |
| 8,778,873 | B2 | 7/2014 | Chaudhary | |
| 2002/0010131 | A1 | 1/2002 | Linsell | |

| 2004/0229775 | A1 | 11/2004 | Linsell et al. | |
| 2014/0260098 | A1 | 9/2014 | Teo et al. | |
| 2017/0239323 | A1 * | 8/2017 | Griffith | A61K 47/02 |

FOREIGN PATENT DOCUMENTS

| CA | 2564112 A1 | 7/2018 | |
| EP | 1278549 | 12/2008 | |
| EP | 2195004 B1 | 6/2010 | |
| IN | 201621000791 A | 5/2016 | |
| JP | 11080021 | 3/1999 | |
| JP | 2008201778 | 9/2008 | |
| WO | 199719690 A1 | 6/1997 | |
| WO | 200182971 A3 | 11/2001 | |
| WO | 0198328 A | 12/2001 | |
| WO | 2005042584 A2 | 5/2005 | |
| WO | 2003080079 A1 | 10/2013 | |
| WO | 2014085526 A1 | 6/2014 | |
| WO | 2014194296 A1 | 12/2014 | |
| WO | WO-2016071495 A1 * | 5/2016 | ............. A61K 38/14 |
| WO | 2017118994 A1 | 7/2017 | |

OTHER PUBLICATIONS

Ferrari et al.; "Vancomycin-Triacetyl Cyclodextrin Interaction Products for Prolonged Drug Delivery"; Pharmaceutical Development and Technology; 13; pp. 65-73; (2008).
International Search Report and Written Opinion: International Application No. PCT/EP2017/060653; International Filing Date May 4, 2017; dated Sep. 12, 2017; 11 pages.
Kang et al.; "Glycopeptide Antibiotics: Structure and Mechanisms of Action"; Journal of Facteriology and Virology; 45(2); pp. 67-78; (2015)
Ngim et al.; "Characterization and Resolution of Reversed Phase HPLC Chromatography Failure Attributed to Sulfobutylether-Beta-Cyclodextrin in a Pharmaceutical Sample Preparation"; Journal of Pharmaceutical and Biomedical Analysis; 49; pp. 660-669; (2009).
Ngim et al.; "Effect of Sulfobutyl Ether Beta-Cyclodextrin Modifier on Selectivity of Reversed Phase HPLC Separations"; Journal of Liquid Chromatography & Related Technologies; 35; pp. 2845-2859; (2012)
Zarif et al.; "Physicochemical Characterization of Vancomycin and its Complexes with Beta-Cyclodextrin"; Biomed Res-India; 23(4); pp. 513-520; (2012)
Gu et al.; "Post-reconstitution Stability of Telavancin with Commonly Used Diluents and Intravenous Infusion Solutions"; Current Therapeutic Research; 77; pp. 105-110; (2015)
Stella et al., "Cyclodextrins", Toxicologic Pathology, 36:30-42, 2008. .

(Continued)

*Primary Examiner* — Jeffrey E. Russel
(74) *Attorney, Agent, or Firm* — McNeill Baur PLLC

(57) ABSTRACT

Disclosed herein are liquid formulations of glycopeptide antibiotics or pharmaceutically acceptable salts thereof, wherein glycopeptide antibiotic is selected from Vancomycin, Telavancin, Oritavancin, Teicoplanin and Dalbavancin.

The formulations are suitable as infusion solutions or as a concentrate for making infusion solutions.

10 Claims, 6 Drawing Sheets

(56) References Cited

OTHER PUBLICATIONS

Diaz et al., "Comparative in vitro study of the antimicrobial activities of different commercial antibiotic products of vancomycin", BMC Clinical Pharmacology, 11:9, 2011.
Ensom et al., Stability of Vancomycin 25 mg/mL in Ora-Sweet and Water in Unit-Dose Cups and Plastic Bottles at 4° C. and 25° C., CJHP, vol. 63, No. 5, Sep.-Oct. 2010.

* cited by examiner

Vancomycin (Formula 1)

Teicoplanin

Telavancin

Oritavancin

Dalbavancin

Formula 3. *DAMS (Des-(amido)-succinimido-Vancomycin B)*

Formula 4a. CDP1 minor

Formula 4b. *CDP1 major*

STABILIZED GLYCOPEPTIDE ANTIBIOTIC FORMULATIONS

CROSS REFERENCE TO RELATED APPLICATIONS

This application is a National Stage application of PCT/EP2017/060653, filed May 4, 2017, which claims the benefit of U.S. Provisional Application No. 62/333,357, filed May 9, 2016.

FIELD OF THE INVENTION

The present invention relates to stable liquid formulations of glycopeptide antibiotics, the use thereof, and process for the preparation of such formulations. Said formulations are suitable as infusion solutions or as a concentrate for making infusion solutions.

Furthermore, it relates to pre-mixed ready-to-use pharmaceutical formulations of glycopeptide antibiotics.

BACKGROUND OF THE INVENTION

Glycopeptide antibiotics are a class of naturally occurring or semi-synthetic antimicrobial agents which act by inhibition of bacterial cell wall biosynthesis and/or membrane integrity.

The best known glycopeptide antibiotics include Vancomycin, Teicoplanin, Oritavancin, Dalbavancin and Telavancin.

All of the named glycopeptides have potent activity against a broad range of Gram-positive organisms, including staphylococci (including methicillin-resistant *Staphylococcus aureus*), *Streptococcus* spp. and *Enterococcus* spp.

Vancomycin (IUPAC name: (3S,6R,7R,11R,23S,26S,30aS,36R,38aR)-44-[2-O-(3-amino-2,3,6-trideoxy-3-C-methyl-α-L-lyxo-hexopyranosyl)-β-D-glucopyranosyloxy]-3-(carbamoylmethyl)-10, 19-dichloro-2, 3, 4, 5, 6, 7, 23, 24, 25, 26, 36, 37, 38, 38a-tetradecahydro-7, 22, 28, 30, 32-pentahydroxy-6-(N-methyl-D-leucyl)-2,5,24,38,39-pentaoxo-1H, 22H-23, 36-(epiminomethano)-8, 11: 18, 21-dietheno-13, 16: 31, 35-di(metheno)[1,6,9]oxadiazacyclohexadecino[4,5-m][10,2,16]benzoxadiazacyclo-tetracosine-26-carboxylic acid), as the most prominent representative of glycopeptide antibiotics, is a tricyclic heptapeptide, derived from *Amycolatopsis orientalis* (formerly *Nocardia orientalis*), with strong bactericidal activity against many Gram-positive bacteria and useful for treatment of resistant and severe infections caused by susceptive strains of methicillin-resistant (β-lactam-resistant) staphylococci.

Vancomycin structure is represented by Formula 1, which is shown in FIG. 1.

In pharmaceutical use, Vancomycin is usually supplied in a form of hydrochloride salt; Vancomycin hydrochloride, represented by the following structural formula:

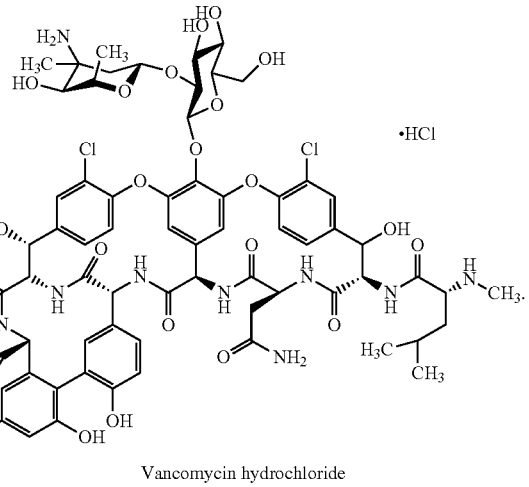

Formula 2

Vancomycin hydrochloride

Vancomycin is currently available in capsule form and in injectable intravenous form, wherein the injectable intravenous products are supplied as a lyophilized powder or as a frozen solution.

Lyophilized powder, prior to administration to a patient, needs to be reconstituted with sterile water for injection (SWI), and further dilution is required. Stability of reconstituted solutions, as well as of diluted ones, is limited even when refrigerated.

Besides limited stability, further disadvantage is that the pH of the diluted formulation varies depending on the choice of the diluent and dilution step additionally includes the potential hazard of contamination, dosage errors and, in the end, potential safety hazard for the patient.

Frozen solutions of Vancomycin, prior to the patient administration, undergo long and inconvenient preparation such as thawing at room temperature or under refrigeration, which is detaining and impractical for medical workers.

Thawed solution is chemically stable for only 72 hours at room temperature or for 30 days when stored under refrigeration.

Identifying lack of chemical and physical stability of Vancomycin as the root cause of all of the above mentioned issues, many attempts have been made to stabilize Vancomycin and related glycopeptide antibiotics in both liquid and solid preparations.

PCT publication WO2014194296 describes Vancomycin-containing compositions which include Vancomycin; propylene glycol or polyethylene glycol, and lactic acid.

U.S. Pat. No. 4,670,258 describes protection of Vancomycin against thermal degradation by mixing certain acetylated dipeptides or tripeptides with Vancomycin in solution in a narrow molar ratio of 1 to 2 moles of peptide to Vancomycin.

WO9719690 describes solutions of Vancomycin HCl comprising 0.5-30% vol/vol ethanol.

JP11080021 described Vancomycin injection suppressed in discoloration, comprising water, Vancomycin and 0.1-10 wt % amino acids (i.e. Glycine).

U.S. Pat. No. 8,778,873 discloses a pharmaceutical composition containing two different antibiotics, a glycopeptide and a cephalosporin, combined with the help of at least one solubilizing/stabilizing agent such as sodium bicarbonate or L-arginine.

US20140260098 disclosure provides a method for a preparation of spray dried Vancomycin hydrochloride powder, wherein excipients selected from stabilizers; solubilizers; a saccharide; a polylol; polyethylene glycol 400; and surfactants are added.

WO2014085526 discloses lipid-based Vancomycin composition, wherein the composition comprises a lipid component, a glycopeptide antibiotic, and an amino acid or a derivative thereof.

WO0182971 discloses pharmaceutical compositions containing a cyclodextrin and a therapeutically effective amount of a glycopeptide antibiotic or a salt thereof.

EP1278549 discloses a pharmaceutical composition comprising a cyclodextrin and a group of glycopeptide antibiotics. The examples involve Telavancin and hydroxypropyl-β-cyclodextrins or sulfobutylether-β-cyclodextrins.

In U.S. Pat. No. 4,885,275, gel-free concentrated aqueous formulations of Vancomycin hydrochloride are provided which comprise the antibiotic salt at a concentration between about 12% and about 50% w/v and a gel-inhibiting compound, e.g., ethanol, at a concentration between about 1% and about 20% v/v.

Japanese application JP2008201778A discloses aqueous Vancomycin preparations with addition of glycerol and D-alanine or DL-alanine and/or D-lactic acid or DL-lactic acid.

Article "Physicochemical characterization of Vancomycin and its complexes with β-cyclodextrin" by Zarif et al., published in *Biomed Res*—India 2012, Volume 23 Issue 4, pages 513-520, describes freeze dried and kneaded compositions comprising β-cyclodextrin and Vancomycin.

Article "Vancomycin-Triacetyl Cyclodextrin Interaction Products for Prolonged Drug Delivery" by Ferrari et al., published in *Pharmaceutical Development and Technology* 2008; 13(1):65-73, describes Vancomycin-Triacetyl cyclodextrin interaction products for prolonged drug delivery.

EP2195004 suggests that Oritavancin may be formulated in 10% hydroxypropyl beta-cyclodextrin.

In *Journal of Liquid Chromatography & Related Technologies*, 2012, 35:2845-2859, article "Effect of sulfobutyl ether beta-cyclodextrin modifier on selectivity of reversed phase HPLC separations" by Ngim et al., discloses a HPLC method involving a sulfobutylether β-cyclodextrin which improved main peak resolution or altered impurity profiles of Vancomycin. The mobile phase contained acetonitrile.

In Ngim et al.: "Characterization and resolution of reversed phase HPLC chromatography failure attributed to sulfobutylether-β-cyclodextrin in a pharmaceutical sample preparation", published in *Journal of Pharmaceutical and Biomedical Analysis*, 49 (2009) 660-669, reversed phase HPLC method failure during analysis of an unknown Vancomycin derivative is disclosed.

U.S. Pat. No. 7,635,773 discloses high-purity sulfoalkyl ether cyclodextrins.

Despite all the effort, none of those listed publications were able to provide pharmaceutical formulations of glycopeptides, especially Vancomycin, in liquid form that show satisfying stability at room temperature for prolonged period of time.

Accordingly, there remains a need for liquid compositions of Vancomycin and related glycopeptides which possess long-term stability under conditions of normal use and storage, and which remain suitable for administration to a subject throughout their stability period.

SUMMARY OF THE INVENTION

The present invention provides liquid pharmaceutical compositions comprising a glycopeptide antibiotic and sulfobutylether-betacyclodextrin, wherein the pharmaceutical compositions are stable for at least about four weeks (1 month) at 25 degrees Celsius in a closed container.

The glycopeptides may be selected from Vancomycin, Telavancin, Oritavancin, Teicoplanin and Dalbavancin.

In one embodiment the glycopeptide is Vancomycin.

The liquid pharmaceutical compositions according to the invention show chemical and physical stability at room temperature. Accordingly, they require no additional steps of preparation, such as, e.g. reconstitution of a lyophilized powder or thawing.

By allowing the use of the composition right off the shelf without any additional preparation, potential contamination problems and dosage errors are prevented.

Furthermore, the liquid pharmaceutical compositions do not require special storage conditions, such as, e.g. freezing or storage in a refrigerator.

The present invention also provides methods for treatment of bacterial infections in a subject, wherein a liquid pharmaceutical composition according to the invention is administered to the subject.

The invention further provides a method for stabilizing glycopeptide antibiotics by mixing the glycopeptide antibiotic with sulfobutylether-beta cyclodextrin in a ratio of glycopeptide antibiotic to sulfobutylether-beta cyclodextrin at which the pharmaceutical solution is stable for at least about four weeks (1 month) at 25 degrees Celsius in a closed container.

The invention also relates to a method of manufacturing liquid pharmaceutical solutions comprising the steps of mixing a glycopeptide antibiotic and sulfobutylether-beta-cyclodextrin in a ratio of glycopeptide antibiotic to sulfobutylether-beta cyclodextrin at which the pharmaceutical solutions are stable for at least about four weeks (1 month) at 25 degrees Celsius in a closed container.

Other objects, features and advantages of the present invention will become apparent from the following detailed description and examples. It should be understood, however, that the detailed description and the examples, while indicating specific embodiments of the invention, are given by way of illustration only and are not intended as a definition of the limits of the invention.

DETAILED DESCRIPTION OF THE INVENTION

Figure 1:
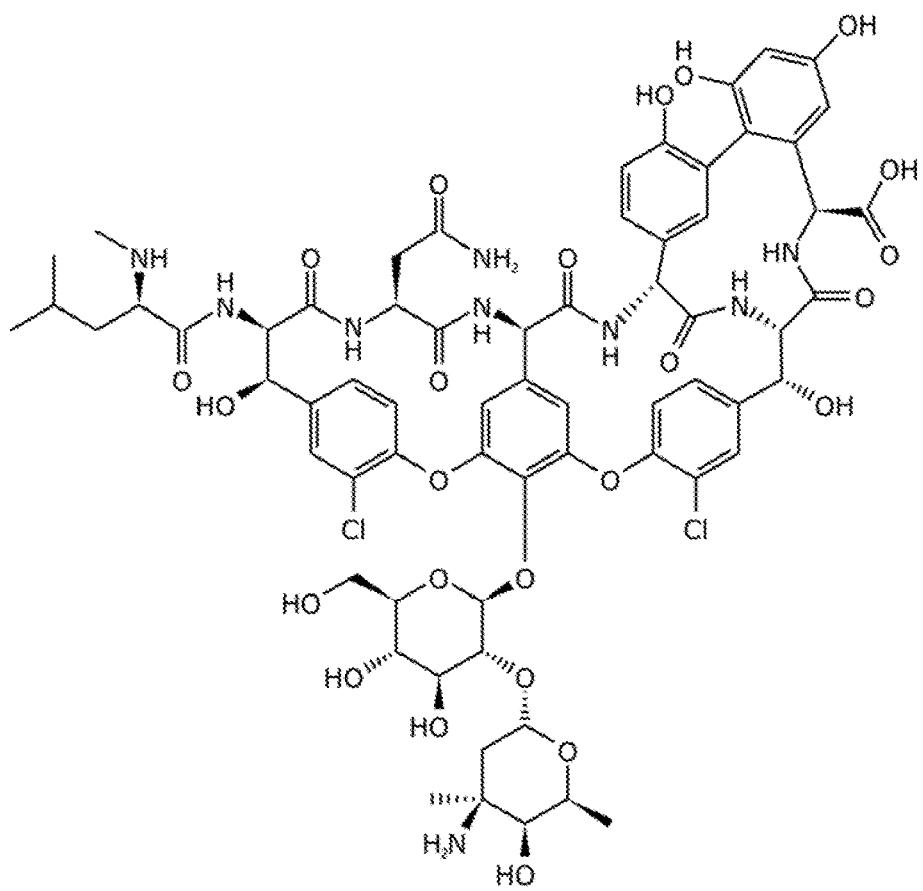
FIG. 1 represents structure formulae of Vancomycin, Teicoplanin, Telavancin Oritavancin and Dalbavancin.
Figure 1:
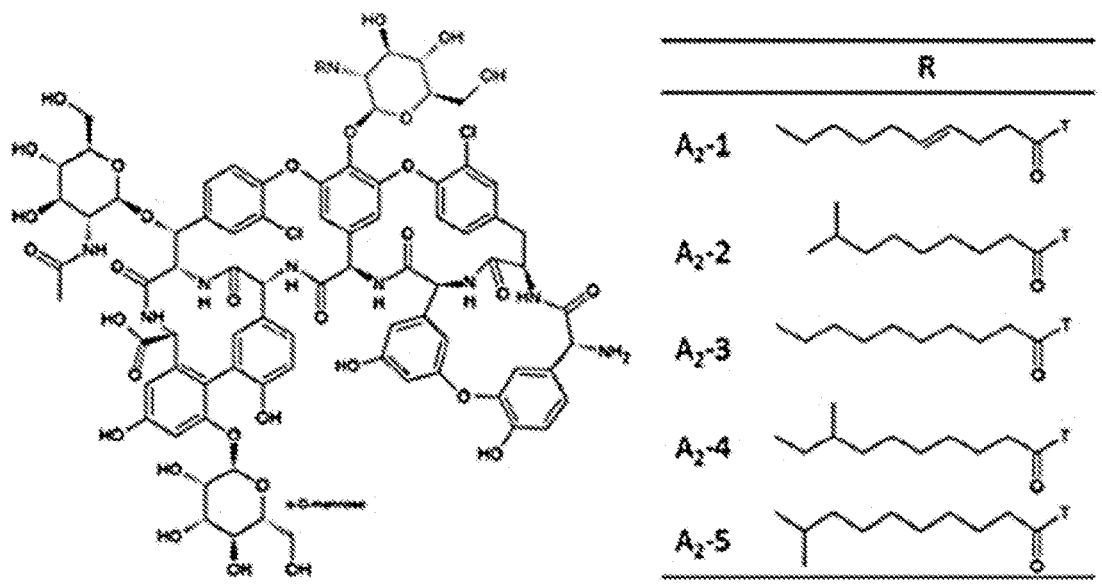
Figure 1:
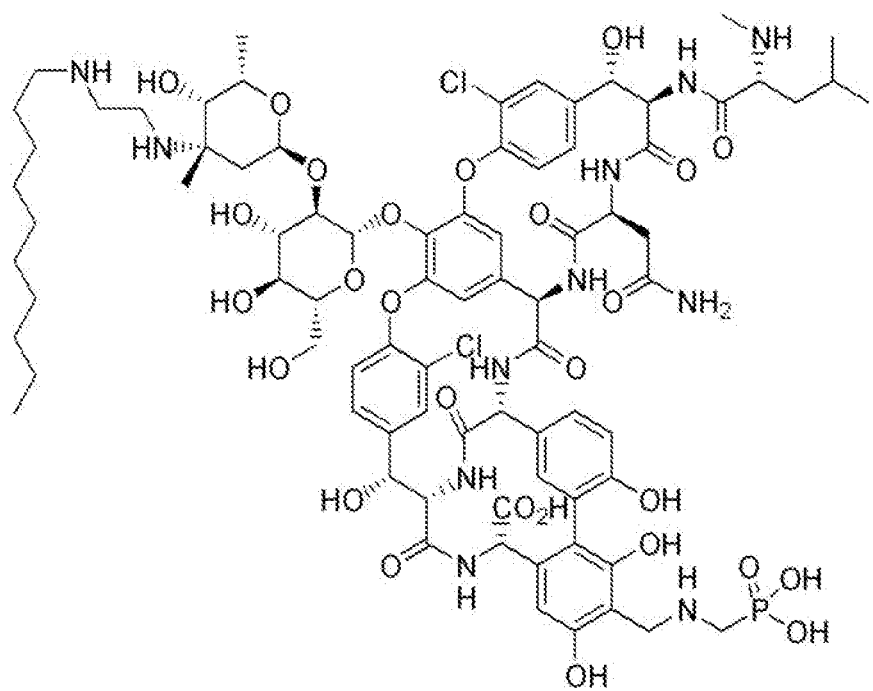
Figure 1:
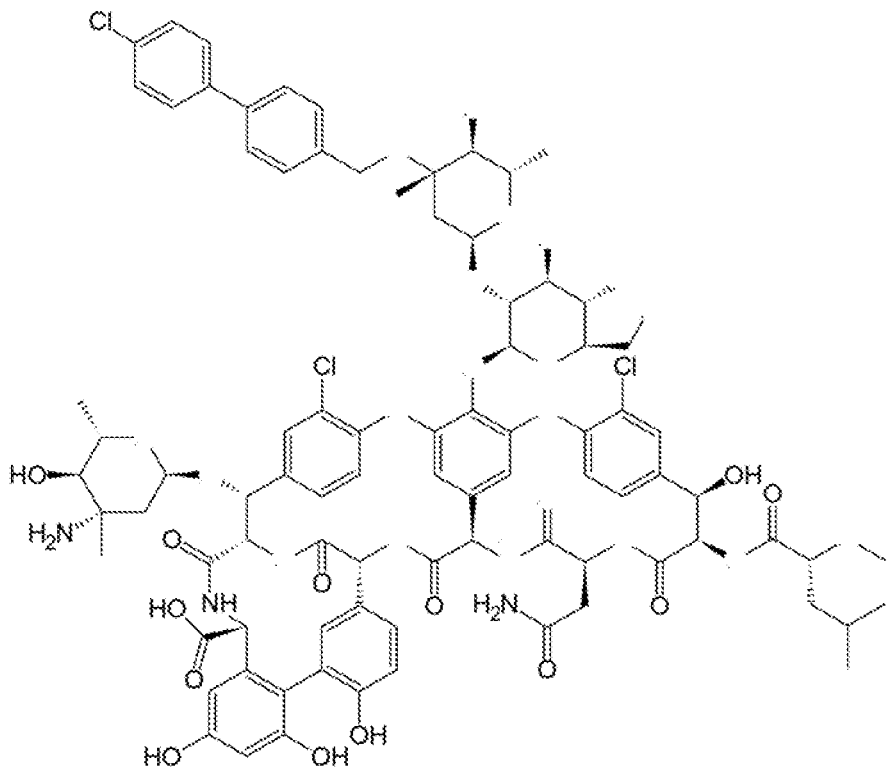
Figure 1:
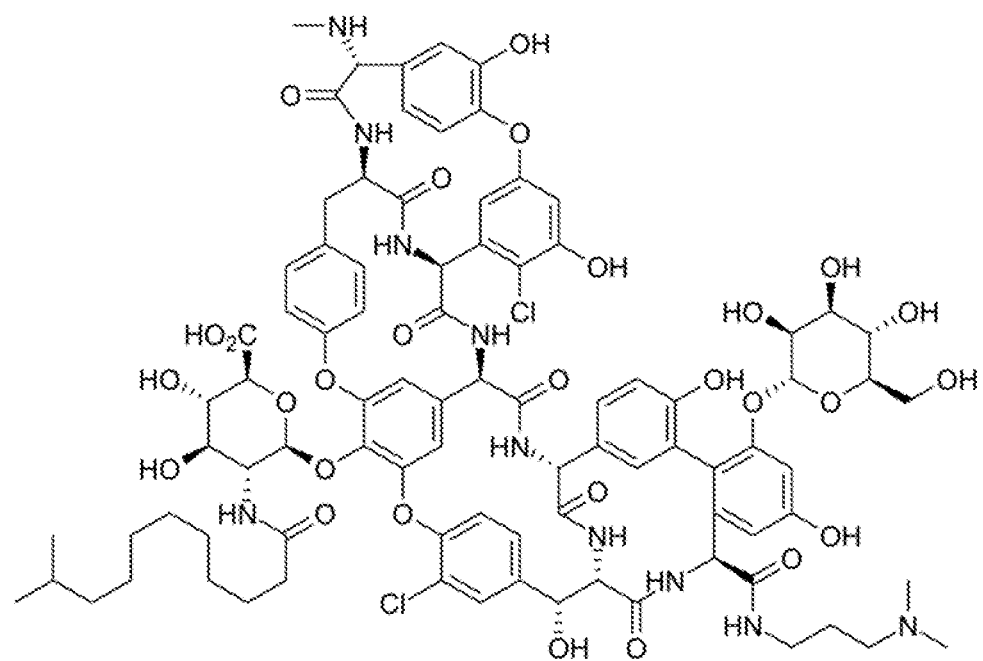

During development of liquid pharmaceutical formulations, maintenance of various chemical and physical properties to preserve the effectiveness and safety of the drug is of crucial importance, since those properties dictate the shelf life of a product, handling, and storage conditions such as temperature, humidity, light etc.

Chemical stability of the active ingredient or degradation of active substance into breakdown products directly affects the uniformity of dosage throughout the shelf life of a product, while physical degradation can lead to various changes in physical state of the formulation due to loss of solvents, precipitation, coloration, and accordingly, has potential impact on chemical stability.

Injectable liquid products, made either from lyophilized powder or already provided as a solution, should meet criteria for physical stability such as acceptable appearance, clarity or color, as well as microbiological standards for pharmaceutical solutions.

Injectable solutions should be essentially free from particles that can be observed on visual inspection, but prevention of formation of aggregates and particulates in solutions continues to be one of the major obstacles and quality concerns in pharmaceutics development.

Packaging also plays an important role in quality maintenance and is very important when drug product stability is being considered. The immediate container and closure are particularly important in affecting product stability, since often physical instability occurs when interaction of the contents with the container and changes in chemical composition take place.

Further, the resistance of packaging materials to, for example moisture and light, can significantly affect the stability of drugs and their dosage forms.

The primary role of packaging, other than its esthetic one, is to protect the dosage forms from moisture and oxygen present in the atmosphere, light, and other types of exposure, especially if these factors affect the overall quality of the product on long-term storage.

Protection from atmospheric conditions can be achieved using primary packaging (packaging that is in direct contact with the dosage forms) and secondary packaging made of for example, moisture and light resistant materials.

The pharmaceutical formulations of glycopeptides, especially Vancomycin, according to this invention, overcome all of the above mentioned disadvantages. In particular, liquid and the pre-mixed ready-to-use, injectable formulations described herein are chemically and physically stable at room temperature, further allow the use of prepared containers right off the shelf without any additional preparation, and consequently, avoid potential contamination problems and eliminate dosage errors. Additionally, formulations according to this invention exhibit both chemical and physical stability when in contact with different packaging materials.

Vancomycin degrades into two main degradation impurities: Des-(amido)-succinimido-Vancomycin B (DAMS), which then converts to Des-(amido)-isoaspartate-Vancomycin B minor/major (CDP1-m/M). The two conformers, CDP-1M and CDP-1m, are usually quantified as one impurity named CDP1.

The pathway of degradation is: Vancomycin→succinimide→CDP-I-m⇌CDP-I-M

In general, related-substance impurities exhibit reduced activity compared to Vancomycin B (the active compound), wherein CDP-1, the rearranged isoaspartic analogue of Vancomycin, has no antibacterial activity.

Figure 2A:
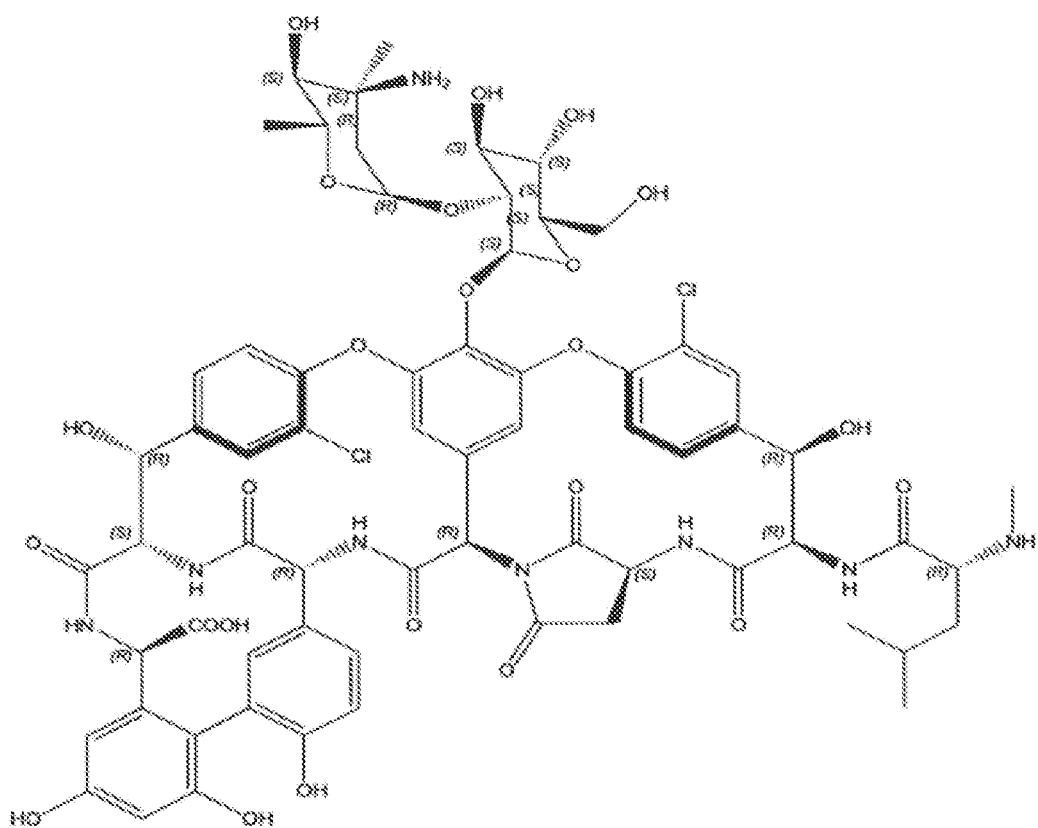
FIGS. 2A-C represent structures of mentioned impurities as Formulas 3, 4a and 4b.
Figure 2B:
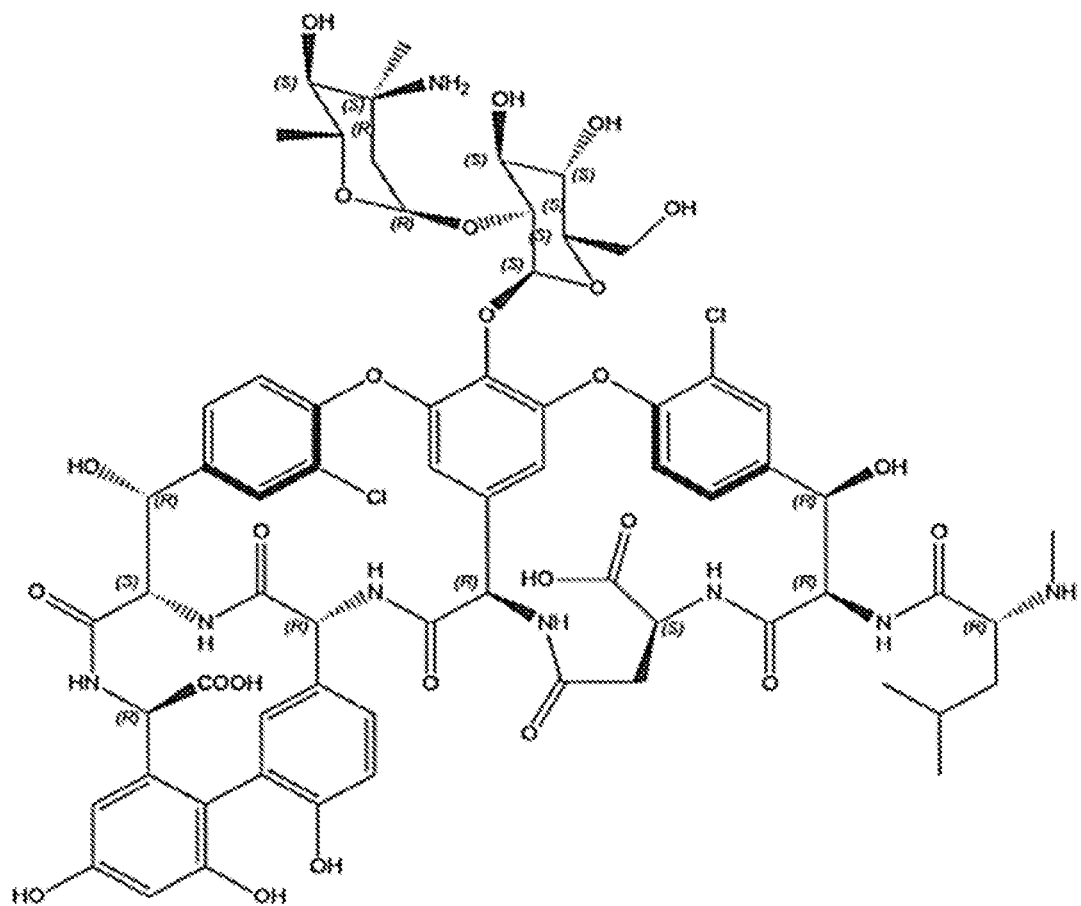
Figure 2C:
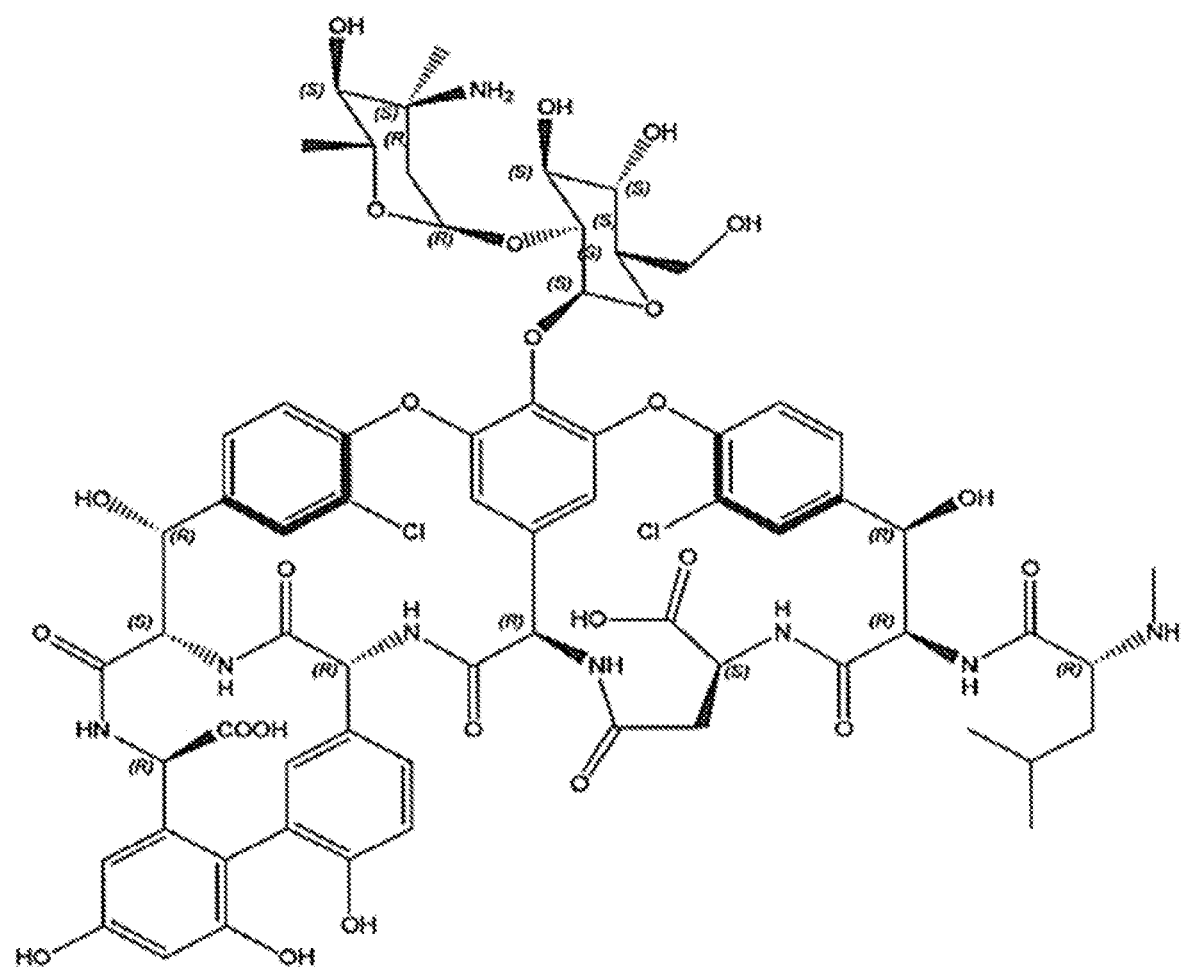

Structures of mentioned impurities are shown in FIGS. 2A-C as Formulas 3, 4a and 4b.

Definitions

"Glycopeptide antibiotics", according to this invention, are meant to embrace molecules which contain a heptapeptide structure providing specific affinity for the D-alanyl-D-Alanine terminus of the peptidoglycan pentapeptide including, for example, Vancomycin, Televancin, Oritavancin, Teicoplanin and Dalbavancin (See Parenti & Cavalleri, *Journal of Antibiotics*, December 1989 page 1882). Structures for some of those molecules are shown in FIG. 1, which is adapted from Kang and Park, *Journal of Bacteriologyand Virology*, 2015 vol. 45 no. 2 pages 67-78.

"Vancomycin", as used herein, means the compound represented by Formula 1, and its pharmaceutically acceptable salts, for example Vancomycin Hydrochloride represented by Formula 2.

Cyclodextrins are a group of cyclic oligosaccharides composed of (α-1,4)-linked α-D-glucopyranose units that contain a somewhat lipophilic central cavity and a hydrophilic outer surface.

β-Cyclodextrins contain seven α-1,4-linked glucose units. The 21 hydroxy groups present in this molecule can be wholly or partly substituted for example with optionally substituted aliphatic $C_2$-$C_6$ groups, preferably with sulfobutyl groups. The cyclodextrins used in this invention preferably have an average degree of substitution per molecule of from 1 to 10, in particular from 3 to 8, such as, from 4 to 8, from 5 to 8 or from 6 to 8.

The term "cyclodextrin" for the purposes of the invention includes the partially and the completely substituted cyclodextrins, especially sulfobutyl-substituted β-cyclodextrins.

"Sulfobutylether β-cyclodextrin", as used in this specification, means any β-cyclodextrin monomer comprising at least one sulfobutylether substituent attached to a hydroxyl group on the cyclodextrin. Sulfobutylether-β-cyclodextrin, in this specification is abbreviated as SBEβ-CD or as CD.

The term "amino acid" includes, but is not limited to the 20 amino acids naturally occurring in peptides in both D and L-form and is also meant to cover any salt thereof, especially pharmaceutically acceptable salts.

For example, the term "amino acid" includes Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, Valine and Ornithine. Thus included is L-Alanine, L-Arginine, L-Asparagine, L-Aspartic acid, L-Cysteine, L-Glutamic acid, L-Glutamine, L-Histidine, L-Isoleucine, L-Leucine, L-Lysine, L-Methionine, L-Phenylalanine, L-Proline, L-Serine, L-Threonine, L-Tryptophan, L-Tyrosine, L-Valine and L-Ornithine; D-Alanine, D-Arginine, D-Asparagine, D-Aspartic acid, D-Cysteine, D-Glutamic acid, D-Glutamine, D-Histidine, D-Isoleucine, D-Leucine, D-Lysine, D-Methionine, D-Phenylalanine, D-Proline, D-Serine, D-Threonine, D-Tryptophan, D-Tyrosine, D-Valine and D-Ornithine.

"N-acetyl-Glycine" is a compound represented by the following structure:

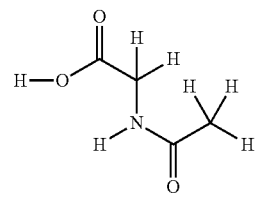

or the compound as indicated by the CAS registry number 543-24-8. It can exist as an acid or in deprotonated form. The term "N-acetyl-Glycine" is also meant to cover any salt thereof, especially pharmaceutically acceptable salts.

"N-acetyl-D-Alanine" is a compound which could be represented by the following structure:

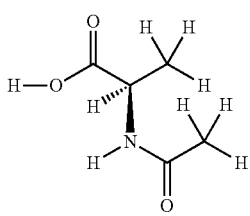

or the compound as indicated by the CAS registry number: 19436-52-3.

It can exist as an acid or in deprotonated form. The term "N-acetyl-D-Alanine" is also meant to cover any salt thereof, especially pharmaceutically acceptable salts. In present specification, N-acetyl-D-Alanine is abbreviated as NADA.

"pH" is the conventional measurement unit of hydrogen ion activity in a solution at room temperature (25° C.) unless other temperature is specified.

A preferred pH range for the formulations of the invention is from about 2.0 to about 6.0; in particular from about 2.5 to about 5.5 and specifically from about 4.5 to about 5.5.

The pH of the glycopeptide antibiotic compositions according to the present invention will be affected by the concentration of each of the ingredients. The pH of the solutions is preferably measured at room temperature.

The pH of the glycopeptide antibiotic solutions according to the present invention can be adjusted in any suitable manner by means of the addition of pH adjusting agents known in the prior art in an amount sufficient to maintain a pH of the compositions from about 2.0 to about 6.0, e.g. by addition of aqueous hydrochloric acid solutions or aqueous sodium hydroxide solutions. Such solutions can be diluted or concentrated. Thus, suitable pH adjusting agents include, but are not limited to 0.01 M HCl, 0.1 M HCl, 1 M HCl, 2 M HCl, 3 M HCl, 4 M HCl, 5 M HCl, 6 M HCl, 0.01 M NaOH, 0.1 M NaOH, 1 M NaOH, 2 M NaOH, 3 M NaOH, 4 M NaOH, 5 M NaOH and 6 M NaOH. Thus, suitable pH adjusting agents include, but are not limited to 0.01-6 M HCl and 0.01-6 M NaOH.

The term "pharmaceutical composition" as used herein, means a composition of glycopeptide antibiotic, for example Vancomycin, that is made under conditions such that it is suitable for administration to a patient and contains pharmaceutically acceptable excipients, e.g. without limitation to solvents, stabilizers, bulking agents, surfactants, buffers, carriers, diluents, vehicles, solubilizers and binders.

"Aqueous composition" as used herein, means any solution in which water is the only solvent or one of the main solvents (equal or above 50% V/V). Aqueous solutions include, but are not limited to solutions comprising 50%, 60%, 70%, 80%, 85%, 90%, 95%, 98%, 99%, 100% V/V water.

The aqueous solutions can additionally comprise pharmaceutically acceptable and physiologically tolerated one or more organic solvents.

The organic solvents, according to this invention, include a glycol—such as polyethylene glycol (PEG 200, PEG 300, PEG 400, PEG 600, PEG 4000 etc.) and propylene glycol, and alcohols such as ethanol, or any mixtures thereof.

"Liquid composition" or "Solution" according to this invention is meant to embrace any liquid form of a formulation no matter if the solvent is one or a mixture of two or more solvents in any suitable concentration, wherein solvent or solvents are selected from the following list:

Water

Organic solvents which include a glycol—such as polyethylene glycol (PEG 200, PEG 300, PEG 400, PEG 600, PEG 4000 etc.) and propylene glycol, and alcohols such as ethanol, and any mixtures thereof Diluents selected from a group consisting of sterile water, bacteriostatic water for injection (BWFI), a pH buffered solution (e.g. phosphate-buffered saline), sterile saline solution, Ringer's solution, dextrose solution, Normosol®-M and ISOLYTE® E, and any mixtures thereof For example: liquid composition formulated in a mixture of 9.6% V/V ethanol in ultrapure water; or formulated in a mixture of 28.8% V/V ethanol and 30% V/V propylene glycol in ultrapure water; or in 55% V/V PEG 400 in ultrapure water; or in 9.6% V/V ethanol in 0.9% NaCl; or in 5.5% V/V PEG 400 in 0.9% NaCl; or in 5.5% PEG 400 in 5% dextrose; or in ultrapure water; or in 0.9% NaCl; etc.

"Liquid compositions comprising Vancomycin HCl" is meant to cover, but not meant to be limited to, solutions made by dissolving Vancomycin HCl, or by addition of equimolar amounts of HCl to Vancomycin base.

As used herein, the terms "pharmaceutical composition", "pharmaceutical formulation", "liquid composition", "liquid formulation", "composition", "formulation" and "solution" are used interchangeably.

Term "stable" here refers to a pharmaceutical formulation containing glycopeptide antibiotic, for example Vancomycin, having sufficient stability to have utility as a pharmaceutical product and meets defined shelf life specifications (chemical and physical stability) for this product as a marketed product.

Preferably, a stable pharmaceutical composition has sufficient stability to allow storage at a convenient temperature, wherein the storage temperature is preferably from 2° C. to 30° C., more preferably from 2° C. to 25° C., for a reasonable period of time, e.g. the shelf-life of the product which can be as short as one month but is typically 12 months or longer.

The language "therapeutically effective amount" of the glycopeptide compound, for example Vancomycin, as used herein, refers to an amount of glycopeptide or its pharmaceutically acceptable salt, for example Vancomycin or pharmaceutically acceptable salt thereof, administered to a patient sufficient to produce a therapeutic response to one or more of the symptoms of the disease being treated.

The term "pharmaceutically acceptable" as used herein, means that it does not cause unacceptable loss of pharmacological activity or unacceptable adverse side effects.

The formulations of the invention may be in the form of premixed infusion solutions ready-to-use or of ready-to-use solution concentrates from which the infusion solution can then be prepared by adding diluent.

"Ready-to-use" refers to compositions that require no reconstitution step.

Term "pre-mixed" refers to a pharmaceutical composition that does not require reconstitution or dilution prior to administration to a patient.

In contrast, the "concentrate solutions" require dilution step prior to use.

The "diluent" of interest herein is one which is pharmaceutically acceptable and is useful for the preparation of a diluted formulation. Exemplary diluents include sterile water, bacteriostatic water for injection (BWFI), a pH buffered solution (e.g. phosphate-buffered saline), sterile saline solution, Ringer's solution, dextrose solution, Normosol®-M and ISOLYTE® E, and any mixtures thereof.

"Sterile" as used in this application means a composition that has been brought to a state of sterility and has not been subsequently exposed to microbiological contamination.

All compositions according to this invention can be provided as sterile compositions, wherein sterilization can be performed by methods well defined and known in the prior art, such as for example filtration sterilization. Sterilized compositions can further be transferred to presterilized containers and sealed.

Described herein are stable pharmaceutical liquid formulations of glycopeptide antibiotics or pharmaceutically acceptable salts thereof, wherein glycopeptide antibiotic is selected from Vancomycin, Telavancin, Oritavancin, Teicoplanin and Dalbavancin.

Liquid formulations of glycopeptide antibiotics according to this invention are provided as stable ready-to-use concentrate formulations which may be diluted prior to administration.

To avoid the inconvenience of diluting a concentrated small volume parenteral formulation into infusion diluents prior to infusion, as well as to eliminate the risk of microbiological contamination during aseptic handling and any potential calculation or dilution error, premixed ready-to-use injectable compositions of glycopeptide antibiotics are also disclosed as a further object of this invention.

Provided stable liquid pharmaceutical compositions, according to this invention, require no additional steps of preparation such as reconstitution of a lyophilized powder, thawing etc. or special storage conditions, for instance, storing at temperatures at or below 0° C.

Provided stable liquid pharmaceutical compositions of glycopeptide antibiotics, according to this invention, show chemical and physical stability when stored at temperatures from 2° C. to 30° C., which is great improvement over the prior art.

Disclosed herein are liquid formulations of glycopeptide antibiotics which are chemically and physically stable for at least about four weeks (1 month) at 2-8° C. (5° C.).

Disclosed herein are liquid formulations of glycopeptide antibiotics which are chemically and physically stable for at least about four weeks (1 month) at 25° C.

Disclosed herein are liquid formulations of glycopeptide antibiotics which are chemically and physically stable for at least about four weeks (1 month) at 30° C.

When stored at 5° C., the pharmaceutical compositions according to the present invention, exhibit between 0% to about 15% loss of the initial purity of the drug and between 0% and to about 10% of two main impurities CDP-1 and DAMS formation independently.

When stored at 25° C., the pharmaceutical compositions according to the present invention, exhibit between 0% to about 15% loss of the initial purity of the drug and between 0% and to about 10% of two main impurities CDP-1 and DAMS formation independently.

When stored at 30° C., the pharmaceutical compositions according to the present invention, exhibit between 0% to about 15% loss of the initial purity of the drug and between 0% and to about 10% of two main impurities CDP-1 and DAMS formation independently.

Further, the present disclosure provides stable liquid pharmaceutical compositions of glycopeptide antibiotics, wherein glycopeptide can be present at concentrations between about 0.1% w/v to about 15% w/V.

Stable liquid pharmaceutical compositions of glycopeptide antibiotics, according to this invention have a pH from about 2.0 to about 6.0.

Stable liquid pharmaceutical compositions of the present invention comprise glycopeptide antibiotic or pharmaceutically acceptable salts thereof as the active ingredient, sulfobutylether β-cyclodextrin as the stabilizing agent, one or a mixture of two or more solvents selected from the group consisting of water, organic solvents and diluents, and optionally one or more excipients selected from a group comprising amino acids such as Glycine, Alanine, Serine, Leucine, Valine, Lysine, Arginine and Ornithine, and/or amino acid derivatives such as N-acetyl-Glycine or N-acetyl-D-Alanine.

According to this invention, organic solvents are selected from a group comprising glycols—such as polyethylene glycol (PEG 200, PEG 300, PEG 400, PEG 600, PEG 4000 etc.) and propylene glycol, and alcohols such as ethanol, and diluents are selected from a group consisting of sterile water, bacteriostatic water for injection (BWFI), a pH buffered solution (e.g. phosphate-buffered saline), sterile saline solution, Ringer's solution, dextrose solution, Normosol®-M and ISOLYTE® E, and any mixtures thereof.

The pharmaceutical compositions described herein can be administered by parenteral routes, well known in the prior art.

The pharmaceutical compositions described herein are useful in treatment of bacterial infections.

Methods for making stable pharmaceutical liquid formulations of glycopeptide antibiotics according to this invention are provided, as well as suitable packaging materials.

According to the invention, the object of providing both chemically and physically stable liquid pharmaceutical formulations of glycopeptide antibiotics at temperatures to about 30° C. is achieved by the following aspects:

In a first aspect, the object is achieved by a liquid formulation comprising Vancomycin or its pharmaceutically acceptable salt and sulfobutylether β-cyclodextrin.

In one embodiment of the first aspect, the liquid formulation comprising Vancomycin or its pharmaceutically acceptable salt and sulfobutylether β-cyclodextrin has a pH from about 2.0 to about 6.0; preferably pH from about 2.5 to about 5.5.

In a second embodiment of the first aspect, the liquid formulation comprising Vancomycin or its pharmaceutically acceptable salt and sulfobutylether β-cyclodextrin has a pH from about 2.5 to about 5.5 and the concentration of Vancomycin or its pharmaceutically acceptable salt ranges from about 0.1% w/V to about 15% w/V, such as, e.g. from about 0.2% w/V to about 15% w/V, from about 0.3% w/V to about 15% w/V, from about 0.4% w/V to about 15% w/V, from about 0.5% w/V to about 15% w/V, from about 0.5% w/V to about 10% w/V, from about 0.5% w/V to about 9% w/V, from about 0.5% w/V to about 8% w/V, from about 0.5% w/V to about 7% w/V, from about 0.5% w/V to about 6% w/V, from about 0.5% w/V to about 5% w/V, from about 1% w/V to about 13% w/V, from about 2% w/V to about 12% w/V, from about 3% w/V to about 11% w/V, from about 4% w/V to about 10% w/V, from about 5% w/V to about 10% w/V, from about 5% w/V to about 9% w/V, from about 5% w/V to about 8% w/V, from about 5% w/V to about 7% w/V and from about 5% w/V to about 6% w/V.

In a third embodiment of the first aspect, the liquid formulation comprising Vancomycin or its pharmaceutically acceptable salt and sulfobutylether β-cyclodextrin has a molar ratio of Vancomycin to SBEβ-CD ranging from about 1:0.5 to about 1:40, such as e.g. from about 1:1 to about 1:30, from about 1:1 to about 1:20, from about 1:1.32 to about 1:20, from about 1:2 to about 1:20, from about 1:3 to about 1:20, from about 1:4 to about 1:20, from about 1:5 to about 1:20, from about 1:6 to about 1:20, from about 1:6.6 to about 1:20.

In a forth embodiment of the first aspect, the liquid formulation comprising Vancomycin or its pharmaceutically acceptable salt and sulfobutylether β-cyclodextrin comprises one or more solvents selected from water, polyethylene glycol 400, propylene glycol, ethanol, and any mixtures thereof.

In a fifth embodiment of the first aspect, the liquid formulation comprises Vancomycin or its pharmaceutically acceptable salt in a concentration of from about 8% w/V to about 11% w/V, such as, e.g. from about 9% w/v to about 10% w/V, sulfobutylether β-cyclodextrin wherein molar ratio of Vancomycin:SBEβ-CD is ranging from about 1:0.5 to about 1:5, such as, e.g. from about 1:1 to 1:4, from about 1:1 to 1:3 and from about 1:1 to about 1:2, one or more solvents selected from water, polyethylene glycol 400, propylene glycol, ethanol and any mixtures thereof, wherein the pH of the solution is from about 2.5 to about 5.5.

In a sixth embodiment of the first aspect, the liquid formulation comprises Vancomycin or its pharmaceutically acceptable salt in a concentration of 10% w/V in a molar ratio to SBEβ-CD ranging from about 1:0.5 to about 1:5, such as, e.g. from about 1:1 to about 1:4, from about 1:1 to about 1:3 and from about 1:1 to about 1:2. In one embodiment the molar ratio is 1:1, 1:1.1, 1:1.2, 1:1.3, 1:1.32, 1:1.4, 1:1.5, 1:1.6, 1:1.7, 1:1.8, 1:1.9, 1:2, 1:2.1, 1:2.2, 1:2.3, 1:2.4, 1:2.5 or 1:3.

In a seventh embodiment of the first aspect, the liquid formulation comprises Vancomycin or its pharmaceutically acceptable salt in a concentration of from about 2% w/V to about 8% w/V, such as, e.g. from about 3% to about 5% w/V, SBEβ-CD wherein molar ratio of Vancomycin:SBEβ-CD ranging from about 1:0.5 to about 1:10, such as, e.g. from about 1:1 to about 1:9, from about 1:1 to about 1:8, from about 1:1 to about 1:7, from about 1:1 to about 1:6, from about 1:1 to about 1:5, from about 1:1 to about 1:4, from about 1:1 to about 1:3, and from about 1:1 to about 1:2, one or more solvents selected from water, polyethylene glycol 400, propylene glycol, ethanol and any mixtures thereof, wherein the pH of the solution is from about 2.5 to about 5.5.

In an eighth embodiment of the first aspect, the liquid formulation comprises Vancomycin or its pharmaceutically acceptable salt in a concentration of 5% w/V in a molar ratio to SBEβ-CD ranging from about 1:0.5 to about 1:10, such as, e.g. from about 1:1 to about 1:9, from about 1:1 to about 1:8, from about 1:1 to about 1:7, from about 1:1 to about 1:6, from about 1:1 to about 1:5, from about 1:1 to about 1:4, from about 1:1 to about 1:3, and from about 1:1 to about 1:2.

In a ninth embodiment of the first aspect, the liquid formulation comprises Vancomycin or its pharmaceutically acceptable salt in a concentration of about 0.1 w/V to about 2% w/V, such as, e.g. from about 0.5% w/v to about 1% w/V, sulfobutylether β-cyclodextrin wherein molar ratio of Vancomycin:SBEβ-CD is ranging from about 1:0.5 to about 1:40, such as from about 1:1 to about 1:30, from about 1:1 to about 1:20, one or more solvents selected from water, polyethylene glycol 400, propylene glycol, ethanol and any mixtures thereof, wherein the pH of the solution is from 2.5 to 5.5.

In a tenth embodiment of the first aspect, the liquid formulation comprises Vancomycin or its pharmaceutically acceptable salt in a concentration of 0.5% w/V in a molar ratio to SBEβ-CD ranging from about 1:0.5 to about 1:40, such as, e.g. from about 1:1 to about 1:30, from about 1:1 to about 1:20 and from about 1:1.32 to about 1:20 In one embodiment the molar ratio is 1:1, 1:1.1, 1:1.2, 1:1.3, 1:1.32, 1:1.4, 1:1.5, 1:1.6, 1:1.7, 1:1.8, 1:1.9, 1:2, 1:2.1, 1:2.2, 1:2.3, 1:2.4, 1:2.5, 1:3, 1:3.1, 1:3.2, 1:3.3, 1:3.4, 1:3.5, 1:4, 1:5, 1:6, 1:6.1, 1:6.2, 1:6.3, 1:6.4, 1:6.5, 1:6.7, 1:6.8, 1:6.9, 1:7, 1:8, 1:9, 1:10, 1:15, 1:16, 1:17, 1:18, 1:19, 1:20, 1:21, 1:22, 1:23, 1:24, 1:25, 1:30, 1:35 or 1:40.

In a eleventh embodiment of the first aspect, the liquid formulation according to any embodiment from one to ten of the first aspect, further comprising one or more diluents selected from sterile water, bacteriostatic water for injection, a pH buffered solution (e.g. phosphate-buffered saline), saline solution, Ringer's solution, dextrose solution, Normosol®-M and ISOLYTE® E.

In a second aspect, the object is achieved by a liquid formulation comprising Vancomycin or its pharmaceutically acceptable salt, sulfobutylether β-cyclodextrin and addition of two or more amino acids selected from Glycine, Alanine, Serine, Leucine, Valine, Lysine, Arginine and Ornithine.

In one embodiment of the second aspect, the liquid formulation comprising Vancomycin or its pharmaceutically acceptable salt, sulfobutylether β-cyclodextrin and two or more amino acids selected from Glycine, Alanine, Serine, Leucine, Valine, Lysine, Arginine and Ornithine has a pH from about 2.0 to about 6.0; preferably pH from about 2.5 to about 5.5.

In a second embodiment of the second aspect, the liquid formulation comprising Vancomycin or its pharmaceutically acceptable salt, sulfobutylether β-cyclodextrin and two or more amino acids selected from D-Alanine, D-Serine, D-Leucine, D-Valine, L-Lysine, D-Lysine, L-Ornithine, D-Ornithine and L-Arginine, has a pH from about 2.0 to about 6.0; preferably pH from about 2.5 to about 5.5.

In a third embodiment of the second aspect, the liquid formulation comprises Vancomycin or its pharmaceutically acceptable salt, sulfobutylether β-cyclodextrin, D-Alanine and L-Lysine, has a pH from about 2.0 to about 6.0; preferably pH from about 2.5 to about 5.5.

In a forth embodiment of the second aspect, the liquid formulation comprising Vancomycin or its pharmaceutically acceptable salt, sulfobutylether β-cyclodextrin and two or more amino acids selected from Glycine, Alanine, Serine, Leucine, Valine, Lysine, Arginine and Ornithine, has a pH from about 2.5 to about 5.5 and the concentration of Vancomycin or its pharmaceutically acceptable salt ranges from about 0.1% w/V to about 15% w/V, such as, e.g. from about 0.2% w/V to about 15% w/V, from about 0.3% w/V to about 15% w/V, from about 0.4% w/V to about 15% w/V, from about 0.5% w/V to about 15% w/V, from about 0.5% w/V to about 10% w/V, from about 0.5% w/V to about 9% w/V, from about 0.5% w/V to about 8% w/V, from about 0.5% w/V to about 7% w/V, from about 0.5% w/V to about 6% w/V, from about 0.5% w/V to about 5% w/V, from about 1% w/V to about 13% w/V, from about 2% w/V to about 12% w/V, from about 3% w/V to about 11% w/V, from about 4% w/V to about 10% w/V, from about 5% w/V to about 10% w/V, from about 5% w/V to about 9% w/V, from about 5% w/V to about 8% w/V, from about 5% w/V to about 7% w/V and from about 5% w/V to about 6% w/V.

In a fifth embodiment of the second aspect, the liquid formulation comprising Vancomycin or its pharmaceutically acceptable salt, sulfobutylether β-cyclodextrin and two or more amino acids selected from D-Alanine, D-Serine, D-Leucine, D-Valine, L-Lysine, D-Lysine, L-Ornithine, D-Ornithine and L-Arginine, has a pH from about 2.5 to about 5.5 and the concentration of Vancomycin or its pharmaceutically acceptable salt ranges from about 0.1% w/V to about 15% w/V, such as, e.g. from about 0.2% w/V to about 15% w/V, from about 0.3% w/V to about 15% w/V, from about 0.4% w/V to about 15% w/V, from about 0.5% w/V to about 15% w/V, from about 0.5% w/V to about 10% w/V, from about 0.5% w/V to about 9% w/V, from about 0.5% w/V to about 8% w/V, from about 0.5% w/V to about 7% w/V, from about 0.5% w/V to about 6% w/V, from about 0.5% w/V to about 5% w/V, from about 1% w/V to about 13% w/V, from about 2% w/V to about 12% w/V, from about 3% w/V to about 11% w/V, from about 4% w/V to about 10% w/V, from about 5% w/V to about 10% w/V, from about 5% w/V to about 9% w/V, from about 5% w/V to about 8% w/V, from about 5% w/V to about 7% w/V and from about 5% w/V to about 6% w/V.

In a sixth embodiment of the second aspect, the liquid formulation comprising Vancomycin or its pharmaceutically acceptable salt, sulfobutylether β-cyclodextrin, D-Alanine and L-Lysine, has a pH from about 2.5 to about 5.5 and the concentration of Vancomycin or its pharmaceutically acceptable salt ranges from about 0.1% w/V to about 15% w/V, such as, e.g. from about 0.2% w/V to about 15% w/V, from about 0.3% w/V to about 15% w/V, from about 0.4% w/V to about 15% w/V, from about 0.5% w/V to about 15% w/V, from about 0.5% w/V to about 10% w/V, from about 0.5% w/V to about 9% w/V, from about 0.5% w/V to about 8% w/V, from about 0.5% w/V to about 7% w/V, from about 0.5% w/V to about 6% w/V, from about 0.5% w/V to about 5% w/V, from about 1% w/V to about 13% w/V, from about 2% w/V to about 12% w/V, from about 3% w/V to about 11% w/V, from about 4% w/V to about 10% w/V, from about 5% w/V to about 10% w/V, from about 5% w/V to about 9% w/V, from about 5% w/V to about 8% w/V, from about 5% w/V to about 7% w/V and from about 5% w/V to about 6% w/V.

In a seventh embodiment of the second aspect, the liquid formulation comprising Vancomycin or its pharmaceutically acceptable salt, sulfobutylether β-cyclodextrin, D-Alanine and L-Lysine has a molar ratio of Vancomycin to SBEβ-CD ranging from about 1:0.5 to about 1:40 and wherein molar ratio of Vancomycin to D-Alanine ranges from about 1:1 to about 1:30 and molar ratio of Vancomycin to L-Lysine ranges from about 1:1 to about 1:30.

In an eighth embodiment of the second aspect, the liquid formulation comprising Vancomycin or its pharmaceutically acceptable salt in a concentration from about 0.1% w/V to about 15% w/V, sulfobutylether β-cyclodextrin, D-Alanine and L-Lysine wherein molar ratio of Vancomycin to SBEβ-CD ranges from about 1:0.5 to about 1:40, molar ratio of Vancomycin to D-Alanine ranges from about 1:1 to about 1:30 and molar ratio of Vancomycin to L-Lysine ranges from about 1:1 to about 1:30, and has pH from about 2.0 to about 6.0; preferably pH from about 2.5 to about 5.5.

In a ninth embodiment of the second aspect, the liquid formulation comprising Vancomycin or its pharmaceutically acceptable salt in a concentration of about 10% w/V, sulfobutylether β-cyclodextrin, D-Alanine and L-Lysine wherein molar ratio of Vancomycin to SBEβ-CD to D-Alanine to L-Lysine is about 1:2:1:1, and pH from about 2.0 to about 6.0; preferably pH from about 2.5 to about 5.5.

In a tenth embodiment of the second aspect, the liquid formulation according to any embodiment from one to nine of the second aspect, comprises one or more solvents selected from water, polyethylene glycol 400, propylene glycol, ethanol, and any mixtures thereof.

In an eleventh embodiment of the second aspect, the liquid formulation according to any embodiment from one to ten of the second aspect, further comprising one or more diluents selected from sterile water, bacteriostatic water for injection, a pH buffered solution (e.g. phosphate-buffered saline), saline solution, Ringer's solution, dextrose solution, Normosol®-M and ISOLYTE® E.

In a third aspect, the object is achieved by a liquid formulation comprising Vancomycin or its pharmaceutically acceptable salt, sulfobutylether β-cyclodextrin and addition of N-acetyl-D-Alanine.

In one embodiment of the third aspect, the liquid formulation comprising Vancomycin or its pharmaceutically acceptable salt, sulfobutylether β-cyclodextrin and N-acetyl-D-Alanine has a pH from about 2.0 to about 6.0; preferably pH from about 2.5 to about 5.5.

In a second embodiment of the third aspect, the liquid formulation comprising Vancomycin or its pharmaceutically acceptable salt, sulfobutylether β-cyclodextrin and N-acetyl-D-Alanine, has a pH from about 2.5 to about 5.5 and the concentration of Vancomycin or its pharmaceutically acceptable salt ranges from about 0.1% w/V to about 15% w/V, such as, e.g. from about 0.2% w/V to about 15% w/V, from about 0.3% w/V to about 15% w/V, from about 0.4% w/V to about 15% w/V, from about 0.5% w/V to about 15% w/V, from about 0.5% w/V to about 10% w/V, from about 0.5% w/V to about 9% w/V, from about 0.5% w/V to about 8% w/V, from about 0.5% w/V to about 7% w/V, from about 0.5% w/V to about 6% w/V, from about 0.5% w/V to about 5% w/V, from about 1% w/V to about 13% w/V, from about 2% w/V to about 12% w/V, from about 3% w/V to about 11% w/V, from about 4% w/V to about 10% w/V, from about 5% w/V to about 10% w/V, from about 5% w/V to about 9% w/V, from about 5% w/V to about 8% w/V, from about 5% w/V to about 7% w/V and from about 5% w/V to about 6% w/V.

In a third embodiment of the third aspect, the liquid formulation comprising Vancomycin or its pharmaceutically acceptable salt, sulfobutylether β-cyclodextrin and N-acetyl-D-Alanine has a molar ratio of Vancomycin to SBEβ-CD ranging from about 1:0.5 to about 1:40 and molar ratio of Vancomycin to N-acetyl-D-Alanine ranging from about 1:1 to about 1:30.

In a forth embodiment of the third aspect, the liquid formulation comprising Vancomycin or its pharmaceutically acceptable salt in a concentration from about 0.1% w/V to about 15% w/V, sulfobutylether β-cyclodextrin, N-acetyl-D-Alanine wherein molar ratio of Vancomycin to SBEβ-CD ranges from about 1:0.5 to about 1:40 and molar ratio of Vancomycin to N-acetyl-D-Alanine ranges from about 1:1 to about 1:30 has pH from about 2.0 to about 6.0; preferably pH from about 2.5 to about 5.5.

In a fifth embodiment of the third aspect, the liquid formulation comprising Vancomycin or its pharmaceutically acceptable salt in a concentration of about 5% w/V, sulfobutylether β-cyclodextrin, N-acetyl-D-Alanine wherein molar ratio of Vancomycin to SBEβ-CD to N-acetyl-D-Alanine is about 1:2.2:2, and has pH from about 2.0 to about 6.0; preferably pH from about 2.5 to about 5.5.

In a sixth embodiment of the third aspect, the liquid formulation according to any embodiment from one to five of the third aspect, comprises one or more solvents selected from water, polyethylene glycol 400, propylene glycol, ethanol, and any mixtures thereof.

In a seventh embodiment of the third aspect, the liquid formulation according to any embodiment from one to six of the third aspect, further comprising one or more diluents selected from sterile water, bacteriostatic water for injection, a pH buffered solution (e.g. phosphate-buffered saline), saline solution, Ringer's solution, dextrose solution, Normosol®-M and ISOLYTE® E.

In a forth aspect, the object is achieved by a liquid formulation comprising Vancomycin or its pharmaceutically acceptable salt, sulfobutylether β-cyclodextrin and addition of N-acetyl-D-Alanine and L-Lysine.

In one embodiment of the forth aspect, the liquid formulation comprising Vancomycin or its pharmaceutically acceptable salt, sulfobutylether β-cyclodextrin, N-acetyl-D-Alanine and L-Lysine has a pH from about 2.5 to about 6.0; preferably pH from about 2.5 to about 5.5.

In a second embodiment of the forth aspect, the liquid formulation comprising Vancomycin or its pharmaceutically acceptable salt, sulfobutylether β-cyclodextrin, N-acetyl-D-Alanine and L-Lysine has a pH from about 2.5 to about 5.5 and the concentration of Vancomycin or its pharmaceutically acceptable salt ranges from about 0.1% w/V to about 15% w/V, such as, e.g. from about 0.2% w/V to about 15% w/V, from about 0.3% w/V to about 15% w/V, from about 0.4% w/V to about 15% w/V, from about 0.5% w/V to about 15% w/V, from about 0.5% w/V to about 10% w/V, from about 0.5% w/V to about 9% w/V, from about 0.5% w/V to about 8% w/V, from about 0.5% w/V to about 7% w/V, from about 0.5% w/V to about 6% w/V, from about 0.5% w/V to about 5% w/V, from about 1% w/V to about 13% w/V, from about 2% w/V to about 12% w/V, from about 3% w/V to about 11% w/V, from about 4% w/V to about 10% w/V, from about 5% w/V to about 10% w/V, from about 5% w/V to about 9% w/V, from about 5% w/V to about 8% w/V, from about 5% w/V to about 7% w/V and from about 5% w/V to about 6% w/V.

In a third embodiment of the forth aspect, the liquid formulation comprising Vancomycin or its pharmaceutically acceptable salt, sulfobutylether β-cyclodextrin, N-acetyl-D-Alanine and L-Lysine has a molar ratio of Vancomycin to SBEβ-CD ranging from about 1:0.05 to about 1:30, such as from about 1:0.05 to about 1:20.

In a forth embodiment of the forth aspect, the liquid formulation comprising Vancomycin or its pharmaceutically acceptable salt, sulfobutylether β-cyclodextrin, N-acetyl-D-Alanine and L-Lysine has a pH from about 2.5 to about 5.5 and the concentration of Vancomycin or its pharmaceutically acceptable salt ranges from about 0.1% w/V to about 15% w/V, such as, e.g. from about 0.2% w/V to about 15% w/V, from about 0.3% w/V to about 15% w/V, from about 0.4% w/V to about 15% w/V, from about 0.5% w/V to about 15% w/V, from about 0.5% w/V to about 10% w/V, from about 0.5% w/V to about 9% w/V, from about 0.5% w/V to about 8% w/V, from about 0.5% w/V to about 7% w/V, from about 0.5% w/V to about 6% w/V, from about 0.5% w/V to about 5% w/V, from about 1% w/V to about 13% w/V, from about 2% w/V to about 12% w/V, from about 3% w/V to about 11% w/V, from about 4% w/V to about 10% w/V, from about 5% w/V to about 10% w/V, from about 5% w/V to about 9% w/V, from about 5% w/V to about 8% w/V, from about 5% w/V to about 7% w/V and from about 5% w/V to about 6% w/V, wherein molar ratio of Vancomycin to SBEβ-CD ranges from about 1:0.05 to about 1:30, such as from about 1:0.05 to about 1:20.

In a fifth embodiment of the forth aspect, the liquid formulation comprises Vancomycin or its pharmaceutically acceptable salt, sulfobutylether β-cyclodextrin, N-acetyl-D-Alanine and L-Lysine, wherein the concentration of Vancomycin is from about 2% w/V to about 10% w/V and the molar ratio of Vancomycin to SBEβ-CD to N-acetyl-D-Alanine to L-Lysine ranges from about 1:0.05:1:1 to about 1:6:5:5, such as e.g. from around 1:0.05:1:1 to around 1:5:4:4, from around 1:0.05:1:1 to around 1:4:3:3, from around 1:0.05:1:1 to around 1:3:2:2.

In a sixth embodiment of the forth aspect, the liquid formulation comprises Vancomycin or its pharmaceutically acceptable salt, sulfobutylether β-cyclodextrin, N-acetyl-D-Alanine and L-Lysine, wherein the concentration of Vancomycin is about 5% w/V and suitable molar ratio of Vancomycin to SBEβ-CD to N-acetyl-D-Alanine to L-Lysine ranges from about 1:0.05:2:2 to about 1:0.1:2:2, such as, e.g. from about 1:0.06:2:2 to about 1:0.09:2:2 and 1:0.07:2:2 to about 1:0.08:2:2, from about 1:0.5:2:2 to about 1:1:2:2, such as, e.g. from about 1:0.6:2:2 to about 1:0.9:2:2 and 1:0.7:2:2 to about 1:0.8:2:2, from about 1:1.1:2:2 to about 1:2:2:2, such as, e.g. from about 1:1.2:2:2 to about 1:1.9:2:2, 1:1.3:2:2 to about 1:1.8:2:2, from about 1:1.4:2:2 to about 1:1.7:2:2 and 1:1.5:2:2 to about 1:1.6:2:2, from about 1:1.6:2:2 to about 1:2.5:2:2, such as, e.g. from about 1:1.7:2:2 to about 1:2.4:2:2, 1:1.8:2:2 to about 1:2.3:2:2, from about 1:1.9:2:2 to about 1:2.2:2:2 and 1:2:2:2 to about 1:2.2:2:2. In one embodiment the ratio is 1:0.067:2:2; 1:0.67:2:2, 1:1.32:2:2; 1:2:2:2; or 1:2.2:2:2.

In a seventh embodiment of the forth aspect, the liquid formulation comprises Vancomycin or its pharmaceutically acceptable salt, sulfobutylether β-cyclodextrin, N-acetyl-D-Alanine and L-Lysine, wherein the concentration of Vancomycin is from about 0.1% w/V to about 2% w/V and the molar ratio of Vancomycin to SBEβ-CD to N-acetyl-D-Alanine to L-Lysine ranges from about 1:0.5:1:1 to about 1:30:30:30, such as e.g. from around 1:0.5:10:10 to around 1:30:30:30.

In an eighth embodiment of the forth aspect, the liquid formulation comprises Vancomycin or its pharmaceutically acceptable salt, sulfobutylether β-cyclodextrin, N-acetyl-D-Alanine and L-Lysine, wherein the concentration of Vancomycin is about 0.5% w/V and suitable molar ratio of Vancomycin to SBEβ-CD to N-acetyl-D-Alanine to L-Lysine ranges from about 1:0.5:20:20 to about 1:1:20:20, such as, e.g. from about 1:0.6:20:20 to about 1:0.9:20:20 and from 1:0.7:20:20 to about 1:0.8:20:20, from about 1:0.5:25:20 to about 1:1:35:20, such as, e.g. from about 1:0.6:30:20 to about 1:0.9:30:20 and from 1:0.7:30:20 to about 1:0.8:30:20, from about 1:5:20:20 to about 1:10:20:20, such as, e.g. from about 1:6:20:20 to about 1:9:20:20 and from 1:7:20:20 to about 1:8:20:20, from about from about 1:5:25:20 to about 1:10:35:20, such as, e.g. from about 1:6:30:20 to about 1:9:30:20 and from 1:7:30:20 to about 1:8:30:20, from about 1:10:20:20 to about 1:30:20:20, such as, e.g. from about 1:15:20:20 to about 1:25:20:20. In one embodiment the ratio is 1:0.67:20:20, 1:0.67:30:20, 1:6.7:20:20, 1:6.7:30:20 or 1:20:20:20.

In a ninth embodiment of the forth aspect, the liquid formulation comprises Vancomycin or its pharmaceutically acceptable salt, sulfobutylether β-cyclodextrin, N-acetyl-D-Alanine and L-Lysine, wherein the concentration of Vancomycin is 5% w/V and the molar ratio of Vancomycin to SBEβ-CD to N-acetyl-D-Alanine to L-Lysine is 1:0.067:2:2, and wherein the pH ranges from about 4.5 to about 5.5.

In a tenth embodiment of the forth aspect, the liquid formulation comprises Vancomycin or its pharmaceutically acceptable salt, sulfobutylether β-cyclodextrin, N-acetyl-D-Alanine and L-Lysine, wherein the concentration of Vancomycin is 0.5% w/V and the molar ratio of Vancomycin to SBEβ-CD to N-acetyl-D-Alanine to L-Lysine is 1:0.67:30:20, and wherein the pH ranges from about 4.5 to about 5.5.

In an eleventh embodiment of the forth aspect, the liquid formulation according to any embodiment from one to ten of the forth aspect, comprises one or more solvents selected from water, polyethylene glycol 400, propylene glycol, ethanol, and any mixtures thereof.

In a twelfth embodiment of the forth aspect, the liquid formulation according to any embodiment from one to eleven of the forth aspect, further comprising one or more diluents selected from sterile water, bacteriostatic water for injection, a pH buffered solution (e.g. phosphate-buffered saline), saline solution, Ringer's solution, dextrose solution, Normosol®-M and ISOLYTE® E.

In a thirteenth embodiment of the forth aspect, the liquid formulation comprises Vancomycin or its pharmaceutically acceptable salt, sulfobutylether β-cyclodextrin, N-acetyl-D-Alanine and L-Lysine, wherein the concentration of Vancomycin is 0.5% w/V and the molar ratio of Vancomycin to SBEβ-CD to N-acetyl-D-Alanine to L-Lysine is 1:0.67:30:20, and wherein the pH ranges from about 4.5 to about 5.5, comprising one or more diluents selected from sterile water, bacteriostatic water for injection, a pH buffered solution (e.g. phosphate-buffered saline), saline solution, Ringer's solution, dextrose solution, Normosol®-M and ISOLYTE® E.

In a fifth aspect, the invention is related to a method for stabilizing a glycopeptide, such as, e.g. Vancomycin, in a liquid pharmaceutical solution, comprising mixing sulfobutylether-beta cyclodextrin and the glycopeptide antibiotic in a ratio of glycopeptide antibiotic to sulfobutylether-beta cyclodextrin at which the pharmaceutical solution is stable for at least about four weeks at 25 degrees Celsius in a closed container.

Using Vancomycin as an example, the compositions or solutions according to this invention may be prepared by the following methods:

In one embodiment of the fifth aspect, the liquid composition in a) may be prepared by dissolving Vancomycin HCL in suitable solvent or mixture of two or more solvents and/or diluents.

In another embodiment of the fifth aspect, the liquid composition in a) may be prepared by the addition of equimolar amounts of HCl to a solution of Vancomycin base.

In one embodiment the method comprises following steps:
a) addition and dissolution of Vancomycin HCL to obtain a liquid composition comprising Vancomycin HCL
b) addition of SBEβ-CD to the solution obtained in a)
c) optionally addition of organic solvents to b)
d) optionally adjusting the pH.

In a further embodiment the method comprises following steps:
a) addition and dissolution of Vancomycin HCL to obtain a liquid composition comprising Vancomycin HCL
b) addition of organic solvents to a)
c) addition of SBEβ-CD to the solution obtained in b)
d) optionally adjusting the pH.

In a further embodiment the method comprises following steps:
a) addition and dissolution of Vancomycin HCL to obtain a liquid composition comprising Vancomycin HCL
b) addition of one or more amino acid or amino acids derivatives to the solution obtained in a)
c) addition of SBEβ-CD to the solution obtained in b)
d) optionally adjusting the pH.

In a further embodiment the method comprises following steps:
a) addition and dissolution of Vancomycin HCL to obtain a liquid composition comprising Vancomycin HCL
b) addition of one or more amino acid or amino acids derivative to the solution obtained in a)
c) optionally addition of organic solvents to b)
d) addition of SBEβ-CD to the solution obtained in c)
e) optionally adjusting the pH.

In a further embodiment one or mixture of two or more solvents are present in any suitable concentration and are selected from group comprising water, organic solvents which include a glycol, such as polyethylene glycol (PEG 200, PEG 300, PEG 400, PEG 600, PEG 4000 etc.) and propylene glycol, and alcohols such as ethanol, and any mixtures thereof and diluents selected from a group consisting of sterile water, bacteriostatic water for injection (BWFI), a pH buffered solution (e.g. phosphate-buffered saline), sterile saline solution, Ringer's solution, dextrose solution, Normosol®-M and ISOLYTE® E, and any mixtures thereof.

In a sixth aspect, the object is achieved by a liquid formulation according to any of the above aspects and embodiments, wherein liquid formulations can be prepared into small volume parenteral and large volume parenteral dosage forms.

In one embodiment of the sixth aspect, liquid formulations can be stored in any suitable container, wherein suitable containers include vials, Blow-Fill-Seal, ampules, syringes, bags and bottles with sizes ranging from 1 mL to 500 mL, and containers may be fabricated from glass or from polymeric materials.

In a second embodiment of the sixth aspect, liquid formulations can be stored in vials, Blow-Fill-Seal, ampules, syringes, bags and bottles fabricated from glass or from polymeric materials, wherein polymeric materials include polyethylene, polyolefin, polypropylene and polyvinyl chloride.

In a third embodiment of the sixth aspect, liquid formulations stored in vials, Blow-Fill-Seal, ampules, syringes, bags and bottles fabricated from glass or from polymeric materials are further provided with a moisture barrier as a secondary packing system to prevent the loss of solvents during storage and to further ensure the stability of the formulation wherein moisture barrier is an aluminum overwrap.

In a forth embodiment of the sixth aspect, liquid formulations can be stored in vials, Blow-Fill-Seal, ampules, syringes, bags and bottles fabricated from glass or from polymeric materials, wherein polymeric materials include polyethylene, polyolefin, polypropylene and polyvinyl chloride and the formulations are chemically and physically stable for at least four weeks at temperatures up to 30° C.

In a fifth embodiment of the sixth aspect, liquid formulations comprise Vancomycin in a concentration of about 0.5% w/V and are stored in bags made from polymeric materials, wherein polymeric materials include polyethylene, polyolefin, polypropylene and polyvinyl chloride and the formulations are chemically and physically stable for at least four weeks at temperatures up to 30° C.

In a further embodiment liquid compositions comprise about 0.5% w/V of Vancomycin, SBEβ-CD, N-acetyl-D-Alanine and L-Lysine in a molar ratio Van:CD:NADA:LYS of 1:0.67:30:20, wherein the pH of the composition ranges from about 4.5 to about 5.5 and are stored in bags made from polymeric materials, wherein polymeric materials include polyethylene, polyolefin, polypropylene and polyvinyl chloride and the formulations are chemically and physically stable for at least four weeks at temperatures up to 30° C.

In a further embodiment liquid compositions comprise about 0.5% w/V of Vancomycin, SBEβ-CD, N-acetyl-D-Alanine and L-Lysine in a molar ratio Van:CD:NADA:LYS of 1:0.67:30:20, wherein the pH of the composition ranges from about 4.5 to about 5.5, and the solvent is selected from sterile water, bacteriostatic water for injection, a pH buffered solution (e.g. phosphate-buffered saline), saline solution, Ringer's solution, dextrose solution, Normosol®-M and ISOLYTE® E, or mixtures thereof and are stored in bags made from polymeric materials, wherein polymeric materials include polyethylene, polyolefin, polypropylene and polyvinyl chloride and the formulations are chemically and physically stable for at least four weeks at temperatures up to 30° C.

In a further embodiment liquid compositions comprise about 0.5% w/V of Vancomycin, N-acetyl-D-Alanine and L-Lysine in a molar ratio Van:NADA:LYS of 1:30:20, wherein the pH of the composition ranges from about 4.5 to about 5.5 and are stored in bags made from polymeric materials, wherein polymeric materials include polyethylene, polyolefin, polypropylene and polyvinyl chloride and the formulations are chemically and physically stable for at least four weeks at temperatures up to 30° C.

In a further embodiment liquid compositions comprise about 0.5% w/V of Vancomycin, N-acetyl-D-Alanine and L-Lysine in a molar ratio Van:NADA:LYS of 1:30:20, wherein the pH of the composition ranges from about 4.5 to about 5.5, and the solvent is selected from sterile water, bacteriostatic water for injection, a pH buffered solution (e.g. phosphate-buffered saline), saline solution, Ringer's solution, dextrose solution, Normosol®-M and ISOLYTE® E, or mixtures thereof and are stored in bags made from polymeric materials, wherein polymeric materials include polyethylene, polyolefin, polypropylene and polyvinyl chloride and the formulations are chemically and physically stable for at least four weeks at temperatures up to 30° C.

In a further embodiment liquid compositions comprise about 0.5% w/V of Vancomycin, N-acetyl-D-Alanine and L-Lysine in a molar ratio Van:NADA:LYS of 1:30:20, wherein the pH of the composition ranges from about 4.5 to about 5.5, and the solvent is selected from sterile water, bacteriostatic water for injection, a pH buffered solution (e.g. phosphate-buffered saline), saline solution, Ringer's solution, dextrose solution, Normosol®-M and ISOLYTE® E or mixtures thereof, and additionally comprise polyethylene glycol 400 and are stored in bags made from polymeric materials, wherein polymeric materials include polyethylene, polyolefin, polypropylene and polyvinyl chloride and the formulations are chemically and physically stable for at least four weeks at temperatures up to 30° C.

In a further embodiment liquid compositions comprise about 0.5% w/V of Vancomycin, N-acetyl-D-Alanine and L-Lysine in a molar ratio Van:NADA:LYS of 1:30:20, wherein the pH of the composition ranges from about 4.5 to about 5.5, and the solvent is selected from sterile water, bacteriostatic water for injection, a pH buffered solution (e.g. phosphate-buffered saline), saline solution, Ringer's solution, dextrose solution, Normosol®-M and ISOLYTE® E or mixtures thereof, and additionally comprise polyethylene glycol 400 in a concentration of 1.8% V/V and are stored in bags made from polymeric materials, wherein polymeric materials include polyethylene, polyolefin, polypropylene and polyvinyl chloride and the formulations are chemically and physically stable for at least four weeks at temperatures up to 30° C.

In a further embodiment, liquid formulations according to any of the above mentioned embodiments are further provided with a moisture barrier as a secondary packing system to prevent the loss of solvents during storage and to further ensure the stability of the formulation wherein moisture barrier is an aluminum overwrap.

In a further embodiment suitable bags made from polymeric materials, wherein polymeric materials include polyethylene, polyolefin, polypropylene and polyvinyl chloride are bags such as Technoflex PP IV bags, Technoflex PE IV bags, Renolit PE IV bags, Polycine PP IV bags, Sealed Air PE IV bags.

In a seventh aspect, the object is achieved by a liquid formulation according to any of the above aspects and embodiments, wherein liquid formulations are suitable for parenteral administration.

In one embodiment of the seventh aspect, liquid formulation is useful for treatment of bacterial infections.

According to this invention, following numbered embodiments are also included:

1. A liquid pharmaceutical composition comprising a glycopeptide antibiotic and sulfobutylether-betacyclodextrin, wherein the pharmaceutical composition is stable for at least about four weeks at 25° C. in a closed container.
2. The pharmaceutical composition of embodiment 1, wherein the pharmaceutical composition is stable for at least about ten weeks at 25 degrees Celsius in a closed container.
3. The pharmaceutical composition of embodiment 1, wherein the pharmaceutical composition is stable for at least about twelve weeks at 25 degrees Celsius in a closed container.
4. The pharmaceutical composition of embodiment 1, wherein the pharmaceutical composition is chemically stable or physically stable.
5. The pharmaceutical composition of embodiment 1, having a pH of about 2.0 to about 6.0.
6. The pharmaceutical composition of embodiment 1, wherein the glycopeptide antibiotic is Vancomycin, Teicoplanin, Televancin, Dalbavancin or Oritavancin.
7. The pharmaceutical composition of embodiment 6, wherein the glycopeptide antibiotic is Vancomycin.
8. The pharmaceutical composition of embodiment 1, wherein the concentration of the glycopeptide antibiotic is between about 0.1% w/V and 15% w/V.
9. The pharmaceutical composition of embodiment 8, wherein the concentration of the glycopeptide antibiotic is about 0.5 w/V, 5% w/V or 10% w/V.
10. The pharmaceutical composition of embodiment 1, further comprising an organic solvent.
11. The pharmaceutical composition of embodiment 10, wherein the organic solvent comprises ethanol, propylene glycol or polyethylene glycol, or combinations thereof.
12. The pharmaceutical composition of embodiment 11, wherein the organic solvent comprises ethanol and propylene glycol or polyethylene glycol.
13. The pharmaceutical composition of embodiment 11 or 12, wherein the polyethylene glycol has a number average molecular weight of 400.
14. The pharmaceutical composition of embodiment 1, further comprising an excipient selected from N-acetyl-D-Alanine or N-acetyl-Glycine.
15. The pharmaceutical composition of embodiment 14, further comprising an amino acid.
16. A pharmaceutical composition according to embodiment 15, wherein the amino acid is selected from D-Alanine, D-Serine, D-Leucine, D-Valine, L-Lysine, D-Lysine, L-Ornithine, D-Ornithine or L-Arginine.
17. The pharmaceutical composition of embodiment 1, wherein the glycopeptide antibiotic and sulfobutylether-betacyclodextrin are present in any suitable ratio.
18. The pharmaceutical composition of embodiment 17, wherein the glycopeptide antibiotic and sulfobutylether-betacyclodextrin are present in a ratio of about 1:0.5 to 1:40 of glycopeptide antibiotic:sulfobutylether-betacyclodextrin.

19. The pharmaceutical composition of embodiment 18, wherein the glycopeptide antibiotic and sulfobutylether-betacyclodextrin are present in a ratio of 1:1 to about 1:30, from about 1:1 to about 1:20, from about 1:1.32 to about 1:20, from about 1:2 to about 1:20, from about 1:3 to about 1:20, from about 1:4 to about 1:20, from about 1:5 to about 1:20, from about 1:6 to about 1:20, from about 1:6.6 to about 1:20 or ratios such as 1:1, 1:1.1, 1:1.2, 1:1.3, 1:1.32, 1:1.4, 1:1.5, 1:1.6, 1:1.7, 1:1.8, 1:1.9, 1:2, 1:2.1, 1:2.2, 1:2.3, 1:2.4, 1:2.5, 1:3, 1:3.3, 1:4, 1:5, 1:6, 1:6.5, 1:6.6, 1:6.7, 1:6.8, 1:7, 1:8, 1:9, 1:10 or 1:20 of glycopeptide antibiotic:sulfobutylether-betacyclodextrin.

20. The pharmaceutical composition of embodiment 14, wherein the glycopeptide antibiotic, sulfobutylether-betacyclodextrin and N-acetyl-D-Alanine are present in any suitable ratio.

21. The pharmaceutical composition of embodiment 20, wherein the glycopeptide antibiotic, sulfobutylether-betacyclodextrin and N-acetyl-D-Alanine are present in a ratio of about 1:2.2:2 glycopeptide antibiotic:sulfobutylether-betacyclodextrin:N-acetyl-D-Alanine.

22. The pharmaceutical composition of embodiment 15, wherein the glycopeptide antibiotic, sulfobutylether-betacyclodextrin, N-acetyl-D-Alanine and amino acid are present in any suitable ratio.

23. The pharmaceutical composition of embodiment 22, wherein the glycopeptide antibiotic, sulfobutylether-betacyclodextrin and N-acetyl-D-Alanine and amino acid are present in a ratio of about 1:0.067:2:2, 1:0.67:2:2, 1:1.32:2:2, 1:2:2:2, 1:2.2:2:2, 1:0.67:30:20, 1:0.67:20:20, 1:6.7:20:20, 1:6.7:30:20 or 1:20:20:20.

24. The pharmaceutical composition of embodiment 4, wherein the chemical stability is demonstrated by determining the amount of the glycopeptide antibiotic remaining in the pharmaceutical solution after at least about four weeks, and wherein the amount of the glycopeptide antibiotic remaining in the pharmaceutical solution is equal or greater than a predetermined glycopeptide antibiotic amount.

25. A pharmaceutical composition according to embodiment 24, wherein the predetermined glycopeptide antibiotic amount is between about 85% and 100% of the glycopeptide antibiotic initially present.

26. The pharmaceutical composition of embodiment 4, wherein the physical stability is demonstrated by the substantial absence of turbidity or particulate matter in the pharmaceutical composition upon visual inspection.

27. The pharmaceutical composition of embodiment 1, wherein stability is demonstrated by determining the antibiotic activity level of the pharmaceutical solution after at least about four weeks, and wherein the antibiotic activity level is equal or greater than a predetermined antibiotic activity level.

28. The pharmaceutical composition of embodiment 27, wherein the glycopeptide antibiotic is Vancomycin and the predetermined antibiotic activity level is expressed as the minimum inhibitory concentration against *Staphylococcus aureus* ATCC 29213, *Enterococcus faecalis* ATCC 29212 or *Streptococcus pnemoniae* ATCC 49619.

29. The pharmaceutical composition of embodiment 28, wherein the antibiotic activity level is determined according to Clinical and Laboratory Standards Institute (CLSI) guideline M100-S23/S24; M07-A9.

30. The pharmaceutical composition of embodiment 15, wherein the concentration of the glycopeptide antibiotic is about 0.5% w/V, the glycopeptide antibiotic, sulfobutylether-betacyclodextrin, N-acetyl-D-Alanine and amino acid are present in a molar ratio of about 1:0.67:30:20 and the composition has a pH of about 4.5-5.5.

31. The pharmaceutical composition of embodiment 15, wherein the concentration of the glycopeptide antibiotic is about 5% w/V, the glycopeptide antibiotic, sulfobutylether-betacyclodextrin, N-acetyl-D-Alanine and amino acid are present in a molar ratio of about 1:0.067:2:2 and the composition has a pH of about 4.5-5.5.

32. The pharmaceutical composition of embodiment 15, wherein the concentration of the glycopeptide antibiotic is about 10% w/V, the glycopeptide antibiotic, sulfobutylether-betacyclodextrin, N-acetyl-D-Alanine and amino acid are present in a molar ratio of about 1:2:1:1, and the composition further comprises 9.6% v/v ethanol and has a pH of about 4.5-5.5.

33. The pharmaceutical composition of any of embodiment 1-32, wherein the pharmaceutical composition is prepared for parenteral administration.

34. A method for treating bacterial infections in a subject by administering a liquid pharmaceutical composition comprising a glycopeptide antibiotic and sulfobutylether-betacyclodextrin, wherein the pharmaceutical composition is stable for at least about four weeks at 25 degrees Celsius in a closed container.

35. The method of embodiment 34, wherein the pharmaceutical composition is stable for at least about ten weeks at 25 degrees Celsius in a closed container.

36. The method of embodiment 34, wherein the pharmaceutical composition is stable for at least about twelve weeks at 25 degrees Celsius in a closed container.

37. The method of embodiment 34, wherein the pharmaceutical composition is chemically stable or physically stable.

38. The method of embodiment 34, wherein the pharmaceutical formulation has a pH of about 2.0-6.0.

39. The method of embodiment 34, wherein the glycopeptide antibiotic is Vancomycin, Teicoplanin, Telavancin, Dalbavancin or Oritavancin.

40. The method of embodiment 39, wherein the glycopeptide antibiotic is Vancomycin.

41. The method of embodiment 34, wherein the concentration of the glycopeptide antibiotic is between about 0.1 and 15% w/V.

42. The method of embodiment 41, wherein the concentration of the glycopeptide antibiotic is about 0.5 w/V, 5% w/V or 10% w/V.

43. The method of embodiment 34, wherein the pharmaceutical formulation further comprises an organic solvent.

44. The method of embodiment 43, wherein the organic solvent comprises ethanol, propylene glycol or polyethylene glycol, or combinations thereof.

45. The method of embodiment 44, wherein the organic solvent comprises ethanol and propylene glycol or polyethylene glycol.

46. The method of embodiment 44 or 45, wherein the polyethylene glycol has a number average molecular weight of 400.

47. The method of embodiment 34, wherein the pharmaceutical formulation further comprises an excipient selected from N-acetyl-D-Alanine or N-acetyl-Glycine.

48. The method of embodiment 47, wherein the pharmaceutical formulation further comprises an amino acid.

49. The method of embodiment 48, wherein the amino acid is selected from D-Alanine, D-Serine, D-Leucine, D-Valine, L-Lysine, D-Lysine, L-Ornithine, D-Ornithine or L-Arginine.

50. The method of embodiment 34, wherein the glycopeptide antibiotic and sulfobutylether-betacyclodextrin are present in any suitable ratio.

51. The method of embodiment 50, wherein the glycopeptide antibiotic and sulfobutylether-betacyclodextrin are present in a ratio of about 1:0.5 to 1:40 of glycopeptide antibiotic:sulfobutylether-betacyclodextrin.

52. The method of embodiment 51, wherein the glycopeptide antibiotic and sulfobutylether-betacyclodextrin are present in a ratio of 1:1 to about 1:30, from about 1:1 to about 1:20, from about 1:1.32 to about 1:20, from about 1:2 to about 1:20, from about 1:3 to about 1:20, from about 1:4 to about 1:20, from about 1:5 to about 1:20, from about 1:6 to about 1:20, from about 1:6.6 to about 1:20 or ratios such as 1:1, 1:1.1, 1:1.2, 1:1.3, 1:1.32, 1:1.4, 1:1.5, 1:1.6, 1:1.7, 1:1.8, 1:1.9, 1:2, 1:2.1, 1:2.2, 1:2.3, 1:2.4, 1:2.5, 1:3, 1:3.3, 1:4, 1:5, 1:6, 1:6.5, 1:6.6, 1:6.7, 1:6.8, 1:7, 1:8, 1:9, 1:10 or 1:20 of glycopeptide antibiotic:sulfobutylether-betacyclodextrin.

53. The method of embodiment 47, wherein the glycopeptide antibiotic, sulfobutylether-betacyclodextrin and N-acetyl-D-Alanine are present in any suitable ratio.

54. The method of embodiment 53, wherein the glycopeptide antibiotic, sulfobutylether-betacyclodextrin and N-acetyl-D-Alanine are present in a ratio of about 1:2.2:2 glycopeptide antibiotic:sulfobutylether-betacyclodextrin:N-acetyl-D-Alanine.

55. The method of embodiment 48, wherein the glycopeptide antibiotic, sulfobutylether-betacyclodextrin, N-acetyl-D-Alanine and amino acid are present in any suitable ratio.

56. The method of embodiment 55, wherein the glycopeptide antibiotic, sulfobutylether-betacyclodextrin and N-acetyl-D-Alanine and amino acid are present in a ratio of about 1:0.067:2:2, 1:0.67:2:2, 1:1.32:2:2, 1:2:2:2, 1:2.2:2:2, 1:0.67:30:20, 1:0.67:20:20, 1:6.7:20:20, 1:6.7:30:20 or 1:20:20:20.

57. The method of embodiment 37, wherein the chemical stability is demonstrated by determining the amount of the glycopeptide antibiotic remaining in the pharmaceutical solution after at least about four weeks, and wherein the amount of the glycopeptide antibiotic remaining in the pharmaceutical solution is equal or greater than a predetermined glycopeptide antibiotic amount.

58. The method of embodiment 57, wherein the predetermined glycopeptide antibiotic amount is between about 85% and 100% of the glycopeptide antibiotic initially present.

59. The method of embodiment 37, wherein the physical stability is demonstrated by the substantial absence of turbidity or particulate matter in the pharmaceutical composition upon visual inspection.

60. The method of embodiment 34, wherein stability is demonstrated by determining the antibiotic activity level of the pharmaceutical solution after at least about four weeks, and wherein the antibiotic activity level is equal or greater than a predetermined antibiotic activity level.

61. The method of embodiment 60, wherein the glycopeptide antibiotic is Vancomycin, and the predetermined antibiotic activity level is expressed as the minimum inhibitory concentration against *Staphylococcus aureus* ATCC 29213, *Enterococcus faecalis* ATCC 29212 or *Streptococcus pneumoniae* ATCC 49619.

62. The method of embodiment 61, wherein the antibiotic activity level is determined according to Clinical and Laboratory Standards Institute (CLSI) guideline M100-S23/524; M07-A9.

63. The method of embodiment 48, wherein the concentration of the glycopeptide antibiotic is about 0.5% w/V, the glycopeptide antibiotic, sulfobutylether-betacyclodextrin, N-acetyl-D-Alanine and amino acid are present in a molar ratio of about 1:0.67:30:20 and the composition has a pH of about 4.5-5.5.

64. The method of embodiment 48, wherein the concentration of the glycopeptide antibiotic is about 5% w/V, the glycopeptide antibiotic, sulfobutylether-betacyclodextrin, N-acetyl-D-Alanine and amino acid are present in a molar ratio of about 1:0.067:2:2 and the composition has a pH of about 4.5-5.5.

65. The method of embodiment 48, wherein the concentration of the glycopeptide antibiotic is about 10% w/V, the glycopeptide antibiotic, sulfobutylether-betacyclodextrin, N-acetyl-D-Alanine and amino acid are present in a molar ratio of about 1:2:1:1, and wherein the composition further comprises 9.6% v/v ethanol and has a pH of about 4.5-5.5.

66. The method of any of the embodiments 34-65, wherein the pharmaceutical composition is prepared for parenteral administration.

67. The method of embodiment 66, wherein the glycopeptide antibiotic in the pharmaceutical composition administered to the subject is present in an amount sufficient to treat the bacterial infection.

68. A method for stabilizing a glycopeptide antibiotic in a liquid pharmaceutical solution comprising mixing sulfobutylether-beta cyclodextrin and the glycopeptide antibiotic in a ratio of glycopeptide antibiotic to sulfobutylether-beta cyclodextrin at which the pharmaceutical solution is stable for at least about four weeks at 25 degrees Celsius in a closed container.

69. The method of embodiment 68, wherein the pharmaceutical composition is stable for at least about ten weeks at 25 degrees Celsius in a closed container.

70. The method of embodiment 68, wherein the pharmaceutical composition is stable for at least about twelve weeks at 25 degrees Celsius in a closed container.

71. The method of embodiment 68, wherein the pharmaceutical composition is chemically stable or physically stable.

72. The method of embodiment 68, wherein the pharmaceutical formulation has a pH of about 2.0-6.0.

73. The method of embodiment 68, wherein the glycopeptide antibiotic is Vancomycin, Teicoplanin, Telavancin, Dalbavancin or Oritavancin.

74. The method of embodiment 73, wherein the glycopeptide antibiotic is Vancomycin.

75. The method of embodiment 68, wherein the concentration of the glycopeptide antibiotic is between about 0.1 and 15% w/V.

76. The method of embodiment 75, wherein the concentration of the glycopeptide antibiotic is about 0.5 w/V, 5% w/V or 10% w/V.

77. The method of embodiment 68, wherein the pharmaceutical formulation further comprises an organic solvent.

78. The method of embodiment 77, wherein the organic solvent comprises ethanol, propylene glycol or polyethylene glycol, or combinations thereof.

79. The method of embodiment 78, wherein the organic solvent comprises ethanol and propylene glycol or polyethylene glycol.

80. The method of embodiments 78 or 79, wherein the polyethylene glycol has a number average molecular weight of 400.

81. The method of embodiment 68, wherein the pharmaceutical formulation further comprises an excipient selected from N-acetyl-D-Alanine or N-acetyl-Glycine.

82. The method of embodiment 81, wherein the pharmaceutical formulation further comprises an amino acid.

83. The method of embodiment 82, wherein the amino acid is selected from D-Alanine, D-Serine, D-Leucine, D-Valine, L-Lysine, D-Lysine, L-Ornithine, D-Ornithine or L-Arginine.

84. The method of embodiment 68, wherein the glycopeptide antibiotic and sulfobutylether-betacyclodextrin are present in a ratio of about 1:0.5 to 1:40 of glycopeptide antibiotic:sulfobutylether-betacyclodextrin.

85. The method of embodiment 84, wherein the glycopeptide antibiotic and sulfobutylether-betacyclodextrin are present in a ratio of 1:1 to about 1:30, from about 1:1 to about 1:20, from about 1:1.32 to about 1:20, from about 1:2 to about 1:20, from about 1:3 to about 1:20, from about 1:4 to about 1:20, from about 1:5 to about 1:20, from about 1:6 to about 1:20, from about 1:6.6 to about 1:20 or ratios such as 1:1, 1:1.1, 1:1.2, 1:1.3, 1:1.32, 1:1.4, 1:1.5, 1:1.6, 1:1.7, 1:1.8, 1:1.9, 1:2, 1:2.1, 1:2.2, 1:2.3, 1:2.4, 1:2.5, 1:3, 1:3.3, 1:4, 1:5, 1:6, 1:6.5, 1:6.6, 1:6.7, 1:6.8, 1:7, 1:8, 1:9, 1:10 or 1:20 of glycopeptide antibiotic:sulfobutylether-betacyclodextrin.

86. The method of embodiment 81, wherein the glycopeptide antibiotic, sulfobutylether-betacyclodextrin and N-acetyl-D-Alanine are present in a ratio of about 1:2,2:2 glycopeptide antibiotic:sulfobutylether-betacyclodextrin:N-acetyl-D-Alanine.

87. The method of embodiment 82, wherein the glycopeptide antibiotic, sulfobutylether-betacyclodextrin, N-acetyl-D-Alanine and amino acid are present in a ratio of about 1:0.067:2:2, 1:0.67:2:2, 1:1.32:2:2, 1:2:2:2, 1:2.2:2:2, 1:0.67:30:20, 1:0.67:20:20, 1:6.7:20:20, 1:6.7:30:20 or 1:20:20:20 glycopeptide antibiotic:sulfobutylether-betacyclodextrin:N-acetyl-D-Alanine:amino acid.

88. The method of embodiment 71, wherein the chemical stability is demonstrated by determining the amount of the glycopeptide antibiotic remaining in the pharmaceutical solution after at least about four weeks, and wherein the amount of the glycopeptide antibiotic remaining in the pharmaceutical solution is equal or greater than a predetermined glycopeptide antibiotic amount.

89. The method of embodiment 88, wherein the predetermined glycopeptide antibiotic amount is between about 85% and 100% of the glycopeptide antibiotic initially present.

90. The method of embodiment 71, wherein the physical stability is demonstrated by the substantial absence of turbidity or particulate matter in the pharmaceutical composition upon visual inspection.

91. The method of embodiment 71, wherein stability is demonstrated by determining the antibiotic activity level of the pharmaceutical solution after at least about four weeks, and wherein the antibiotic activity level is equal or greater than a predetermined antibiotic activity level.

92. The method of embodiment 91, wherein the glycopeptide antibiotic is Vancomycin, and the predetermined antibiotic activity level is expressed as the minimum inhibitory concentration against *Staphylococcus aureus* ATCC 29213, *Enterococcus faecalis* ATCC 29212 or *Streptococcus pneumoniae* ATCC 49619.

93. The method of embodiment 92, wherein the antibiotic activity level is determined according to Clinical and Laboratory Standards Institute (CLSI) guideline M100-S23/S24; M07-A9.

94. The method of embodiment 82, wherein the concentration of the glycopeptide antibiotic is about 0.5% w/V, the glycopeptide antibiotic, sulfobutylether-betacyclodextrin, N-acetyl-D-Alanine and amino acid are present in a molar ratio of about 1:0.67:30:20 and the composition has a pH of about 4.5-5.5.

95. The method of embodiment 82, wherein the concentration of the glycopeptide antibiotic is about 5% w/V, the glycopeptide antibiotic, sulfobutylether-betacyclodextrin, N-acetyl-D-Alanine and amino acid are present in a molar ratio of about 1:0.067:2:2 and the composition has a pH of about 4.5-5.5.

96. The method of embodiment 82, wherein the concentration of the glycopeptide antibiotic is about 10% w/V, the glycopeptide antibiotic, sulfobutylether-betacyclodextrin, N-acetyl-D-Alanine and amino acid are present in a molar ratio of about 1:2:1:1, and the composition further comprises 9.6% v/v ethanol and has a pH of about 4.5-5.5.

97. The method of any of embodiments 68-96, wherein the pharmaceutical composition is prepared for parenteral administration.

98. A method of manufacturing a stable liquid pharmaceutical solution comprising the steps of mixing a glycopeptide antibiotic and sulfobutylether-betacyclodextrin in a ratio of glycopeptide antibiotic to sulfobutylether-beta cyclodextrin at which the pharmaceutical solution is stable for at least about four weeks at 25 degrees Celsius in a closed container.

99. The method of embodiment 98, wherein the pharmaceutical composition is stable for at least about ten weeks at 25 degrees Celsius in a closed container.

100. The method of embodiment 98, wherein the pharmaceutical composition is stable for at least about twelve weeks at 25 degrees Celsius in a closed container.

101. The method of embodiment 98, wherein the pharmaceutical composition is chemically stable or physically stable.

102. The method of embodiment 98, wherein the pharmaceutical formulation has a pH of about 2.0-6.0.

103. The method of embodiment 98, wherein the glycopeptide antibiotic is Vancomycin, Teicoplanin, Telavancin, Dalbavancin or Oritavancin.

104. The method of embodiment 103, wherein the glycopeptide antibiotic is Vancomycin.

105. The method of embodiment 98, wherein the concentration of the glycopeptide antibiotic is between about 0.1% w/V and 15% w/V.

106. The method of embodiment 105, wherein the concentration of the glycopeptide antibiotic is about 0.5 w/V, 5% w/V or 10% w/V.

107. The method of embodiment 106, wherein the pharmaceutical formulation further comprises an organic solvent.

108. The method of embodiment 107, wherein the organic solvent comprises ethanol, propylene glycol or polyethylene glycol, or combinations thereof.

109. The method of embodiment 108, wherein the organic solvent comprises ethanol and propylene glycol or polyethylene glycol.

110. The method of embodiment 108 or 109, wherein the polyethylene glycol has a number average molecular weight of 400.

111. The method of embodiment 98, wherein the pharmaceutical formulation further comprises an excipient selected from N-acetyl-D-Alanine or N-acetyl-Glycine.

112. The method of embodiment 111, wherein the pharmaceutical formulation further comprises an amino acid.

113. The method of embodiment 112, wherein the amino acid is selected from D-Alanine, D-Serine, D-Leucine, D-Valine, L-Lysine, D-Lysine, L-Ornithine, D-Ornithine or L-Arginine.

114. The method of embodiment 98, wherein the glycopeptide antibiotic and sulfobutylether-betacyclodextrin are present in a ratio of about 1:0.5 to 1:40 of glycopeptide antibiotic:sulfobutylether-betacyclodextrin.

115. The method of embodiment 114, wherein the glycopeptide antibiotic and sulfobutylether-betacyclodextrin are present in a ratio of about 1:1 to about 1:30, from about 1:1 to about 1:20, from about 1:1.32 to about 1:20, from about 1:2 to about 1:20, from about 1:3 to about 1:20, from about 1:4 to about 1:20, from about 1:5 to about 1:20, from about 1:6 to about 1:20, from about 1:6.6 to about 1:20 or ratios such as 1:1, 1:1.1, 1:1.2, 1:1.3, 1:1.32, 1:1.4, 1:1.5, 1:1.6, 1:1.7, 1:1.8, 1:1.9, 1:2, 1:2.1, 1:2.2, 1:2.3, 1:2.4, 1:2.5, 1:3, 1:3.3, 1:4, 1:5, 1:6, 1:6.5, 1:6.6, 1:6.7, 1:6.8, 1:7, 1:8, 1:9, 1:10 or 1:20 of glycopeptide antibiotic:sulfobutylether-betacyclodextrin.

116. The method of embodiment 111, wherein the glycopeptide antibiotic, sulfobutylether-betacyclodextrin and N-acetyl-D-Alanine are present in a ratio of about 1:2.2:2 glycopeptide antibiotic:sulfobutylether-betacyclodextrin:N-acetyl-D-Alanine.

117. The method of embodiment 112, wherein the glycopeptide antibiotic, sulfobutylether-betacyclodextrin, N-acetyl-D-Alanine and amino acid are present in a ratio of about 1:0.067:2:2, 1:0.67:2:2, 1:1.32:2:2, 1:2:2:2, 1:2.2:2:2, 1:0.67:30:20, 1:0.67:20:20, 1:6.7:20:20, 1:6.7:30:20 or 1:20:20:20 glycopeptide antibiotic:sulfobutylether-betacyclodextrin:N-acetyl-D-Alanine:amino acid.

118. The method of embodiment 101, wherein the chemical stability is demonstrated by determining the amount of the glycopeptide antibiotic remaining in the pharmaceutical solution after at least about four weeks, and wherein the amount of the glycopeptide antibiotic remaining in the pharmaceutical solution is equal or greater than a predetermined glycopeptide antibiotic amount.

119. The method of embodiment 118, wherein the predetermined glycopeptide antibiotic amount is between about 85% and 100% of the glycopeptide antibiotic initially present.

120. The method of embodiment 101, wherein the physical stability is demonstrated by the substantial absence of turbidity or particulate matter in the pharmaceutical composition upon visual inspection.

121. The method of embodiment 98, wherein stability is demonstrated by determining the antibiotic activity level of the pharmaceutical solution after at least about 4 weeks, and wherein the antibiotic activity level is equal or greater than a predetermined antibiotic activity level.

122. The method of embodiment 121, wherein the glycopeptide antibiotic is Vancomycin, and the predetermined antibiotic activity level is expressed as the minimum inhibitory concentration against *Staphylococcus aureus* ATCC 29213, *Enterococcus faecalis* ATCC 29212 or *Streptococcus pnemoniae* ATCC 49619.

123. The method of embodiment 122, wherein the antibiotic activity level is determined according to Clinical and Laboratory Standards Institute (CLSI) guideline M100-S23/S24; M07-A9.

124. The method of embodiment 112, wherein the concentration of the glycopeptide antibiotic is about 0.5% w/V, the glycopeptide antibiotic, sulfobutylether-betacyclodextrin, N-acetyl-D-Alanine and amino acid are present in a molar ratio of about 1:0.67:30:20 and the composition has a pH of about 4.5-5.5.

125. The method of embodiment 112, wherein the concentration of the glycopeptide antibiotic is about 5% w/V, the glycopeptide antibiotic, sulfobutylether-betacyclodextrin, N-acetyl-D-Alanine and amino acid are present in a molar ratio of about 1:0.067:2:2 and the composition has a pH of about 4.5-5.5.

126. The method of embodiment 112, wherein the concentration of the glycopeptide antibiotic is about 10% w/V, the glycopeptide antibiotic, sulfobutylether-betacyclodextrin, N-acetyl-D-Alanine and amino acid are present in a molar ratio of about 1:2:1:1, and wherein the composition further comprises 9.6% v/v ethanol and has a pH of about 4.5-5.5.

127. The method of any of embodiments 98-126, wherein the pharmaceutical composition is prepared for parenteral administration.

128. A kit comprising the pharmaceutical solution of any of embodiments 1-33.

129. The kit of embodiment 128, further comprising instructions for storage or use of the pharmaceutical solution.

Examples

Stability of formulations, according to this invention, was determined in a number of ways at specified time point, including determination of Vancomycin B content, quantification of the two main impurities—DAMS and CDP-1, by methods well known in the art, as well as visual inspection of color and appearance.

Materials and Methods

The purity of Vancomycin was determined using HPLC method with detection at 280 nm. The levels of two main degradation impurities (DAMS and CDP-1) were also measured by same HPLC method at the same wavelength, and the amounts were calculated according to the total area percent. Following the initial analysis, the formulations were stored for 4 weeks at 2-8° C., at 25° C. and at 30° C., and purity of Vancomycin and content of impurities were measured again using the same HPLC method.

The HPLC conditions used were those disclosed in the European Pharmacopeia 8.0, pages 3525-3527, employing acceptable variations to the conditions as would be understood by those skilled in the art for certain sample, using the following conditions:

Vancomycin B. Liquid chromatography (2.2.29). Use the solutions within 4 h of preparation.

Test solution (a). Dissolve 10.0 mg of the substance to be examined in mobile phase A and dilute to 5.0 mL with mobile phase A.

Test solution (b). Dilute 2.0 mL of test solution (a) to 50.0 mL with mobile phase A.

Test solution (c). Dilute 0.5 mL of test solution (b) to 20.0 mL with mobile phase A.

Reference solution. Dissolve the contents of a vial of Vancomycin hydrochloride CRS in water R and dilute with the same solvent to obtain a solution containing 0.5 mg/mL. Heat at 65° C. for 24 h. Allow to cool.

Column:
    Size: l=0.25 m, Ø=4.6 mm;
    Stationary phase: octadecylsilyl silica gel for chromatography R (5 µm)

Mobile phase:
    Mobile phase A: to 4 mL of triethylamine R add 1996 mL of water R and adjust pH 3.2 with phosphoric acid R; to 920 mL of this solution add 10 mL of tetrahydrofuran R and 70 mL of acetonitrile R;
    Mobile phase B: to 4 mL of triethylamine R add 1996 mL of water R and adjust pH 3.2 with phosphoric acid R; to 700 mL of this solution add 10 mL of tetrahydrofuran R and 290 mL of acetonitrile R;

| Time (min) | Mobile phase A (percent V/V) | Mobile phase B (percent V/V) |
|---|---|---|
| 0-13 | 100 | 0 |
| 13-22 | 100 → 0 | 0 → 100 |

Flow rate: 1.0 mL/min
Detection: spectrophotometer at 280 nm
Injection: 20 μL
System Suitability:
  Resolution: minimum 5.0 between the 2 principal peaks in the chromatogram obtained with the reference solution;
  Signal-to-noise ratio: minimum 5 for the principal peak in the chromatogram obtained with test solution (c);
  Symmetry factor maximum 1.6 for the peak due to Vancomycin in the chromatogram obtained with test solution (b).
  Calculate the percentage content of Vancomycin B hydrochloride using the following expression:

$$\frac{A_b \times 100}{A_b + \left(\frac{A_t}{25}\right)}$$

$A_b$=area of the peak due to Vancomycin B in the chromatogram obtained with test solution (b);
$A_t$=sum of the areas of the peaks due to impurities in the chromatogram obtained 40 with test solution (a).
Related Substances.
  Liquid chromatography (2.2.29) as described in the test for Vancomycin B with the following modifications:
Injection: test solution (a), (b) and (c).
  Calculate the percentage content of each impurity using the following expression:

$$\frac{\left(\frac{A_i}{25}\right) \times 100}{A_b + \left(\frac{A_t}{25}\right)}$$

$A_i$=area of the peak due to an impurity in the chromatogram obtained with test solution (a);
$A_b$=area of the peak due to Vancomycin B in the chromatogram obtained with test solution (b);
$A_t$=sum of the areas of the peaks due to impurities in the chromatogram obtained with test solution (a).
  Antibacterial susceptibility testing can be performed using broth dilution method according to Clinical and Laboratory Standards Institute (CLSI) guidelines M100-S23/S24; M07-A9, the disclosure of which is herein incorporated by reference.
  The antibiotic activity of pharmaceutical compositions according to this invention can be determined and compared to the activity of the injectable reference finished product. Antibiotic activity can be determined against quality control strains: *Staphylococcus aureus* ATCC 29213, *Enterococcus faecalis* ATCC 29212 and *Streptococcus pnemoniae* ATCC 49619.
  In table 1 referent minimum inhibitory concentration (MIC) ranges for evaluation of Vancomycin solution activity against tested quality control strains according to the CLSI protocol are provided.

TABLE 1

Referent minimum inhibitory concentration (MIC) of Vancomycin Referent MIC ranges (μg/mL)

| QC strains | Vancomycin |
|---|---|
| *Staphylococcus aureus* ATCC 29213 | 0.5-2 |
| *Enterococcus faecalis* ATCC 29212 | 1-4 |
| *Streptococcus pnemoniae* ATCC 49619 | 0.125-0.5 |

The formulations of the invention can be prepared simply by mixing and dissolving components. However, three examples of formulations with different compounding procedures, different compositions, different concentrations of individual substances, different molar ratios and different pH adjustment are described below, but for a person skilled in the art it would be apparent from the following examples how to prepare other formulations disclosed in this application:
Example of Concentrate Solutions:
Liquid Compositions Comprising 10% w/V Vancomycin HCl (Final Batch Volume=100 mL):
  10 g of Vancomycin HCl (weight adjusted with respect to API potency) is dissolved in ultrapure water to achieve the final concentration of 100 mg/mL (i.e. 10% w/V solution). After dissolution of Vancomycin, 9.6% V/V of ethanol was added and addition of 19.69 g of SBEβ-CD followed in order to achieve final molar ratio of Vancomycin:cyclodextrin=1:1.32. After components were dissolved and prior batch volume make up, pH of the solution was adjusted to pH around 3.0 with diluted HCl.
Liquid Compositions Comprising 5% w/V Vancomycin HCl (Final Batch Volume=100 mL):
  5 g of Vancomycin HCl (weight adjusted with respect to API potency) is dissolved in ultrapure water to achieve the final concentration of 50 mg/mL (i.e. 5% w/V solution). After dissolution of Vancomycin, 1.260 g of L-Lysine HCl, 0.905 g of N-acetyl-D-Alanine and 0.5 g of SBEβ-CD was added to achieve final molar ratio of Vancomycin:Lysine:N-acetyl-D-Alanine:SBEβ-CD=1:2:2:0.067. After all components were dissolved and prior batch volume make up, pH of the solution was adjusted to pH around 5.0 with diluted NaOH.
  Concentrate solutions containing Vancomycin can be further diluted with suitable diluent prior to the patient administration, wherein diluents are selected from sterile water, bacteriostatic water for injection (BWFI), a pH buffered solution (e.g. phosphate-buffered saline), sterile saline solution, Ringer's solution, dextrose solution, Normosol®-M and ISOLYTE® E, and any mixtures thereof.
Example of a Pre-Mixed Ready-to-Use Infusion Formulation:
Liquid Compositions Comprising 0.5% w/V Vancomycin HCl (Final Batch Volume=100 mL):
  0.5 g of Vancomycin HCl (weight adjusted with respect to API potency) is dissolved in 0.9% NaCl to achieve the final concentration of 5 mg/mL (i.e. 0.5% w/V solution). After dissolution of Vancomycin, 1.260 g of L-Lysine HCl, 1.357 g of N-acetyl-D-Alanine and 0.5 g of SBEβ-CD was added to achieve final molar ratio of Vancomycin:Lysine:N-acetyl-D-Alanine:SBEβ-CD=1:20:30:0.67. After all components were dissolved and prior batch volume make up, pH of the solution was adjusted to pH around 5.0 with diluted NaOH.
  In all of the above and below presented examples L-Lysine was added in a form of L-Lysine monohydrochloride (abbreviated LYS).

In the following tables abbreviations were used in the following manner:

Van—Vancomycin or Vancomycin HCL
SBEβ-CD or CD—Sulfobutylether-betacyclodextrin
ALA—D-Alanine
Lysine or LYS—L-Lysine or L-Lysine monohydrochloride
NADA—N-acetyl-D-Alanine

TABLE 2

Comparative accelerated stability data at 25° C./60% RH and long term stability data at 2-8° C. of Vancomycin liquid formulations containing SBEβ-CD in a mixture of ethanol and ultrapure water

| Composition | Vancomycin conc. | Solvent | Molar ratio Van:CD | pH | Temperature | Time point | Purity % | DAMS % | CDP1 % | Appearance |
|---|---|---|---|---|---|---|---|---|---|---|
| Vancomycin HCl | 10% | Ultrapure water | / | 3.05 | START | START | 96.2 | 0.7 | 0.2 | Clear, colorless solution without visible particles |
| | | | | | 5° C. | 1 M | 95.9 | 1.1 | 0.2 | Clear, mildly yellow solution without visible particles |
| | | | | | 25° C. | 1 M | 87.5 | 4.3 | 5.2 | Clear, mildly yellow solution without visible particles |
| Vancomycin HCl | 10% | 9.6% ethanol (V/V) in ultrapure water | / | 3.02 | START | START | 96.2 | 0.7 | 0.3 | Clear, mildly yellow solution without visible particles |
| | | | | | 5° C. | 1 M | 96.0 | 0.9 | 0.3 | Clear, mildly yellow solution without visible particles |
| | | | | | 25° C. | 1 M | 89.4 | 4.0 | 3.4 | Clear, mildly yellow solution without visible particles |
| Vancomycin HCl + SBEβ-CD | 10% | 9.6% ethanol (V/V) in ultrapure water | 1:1 | 3.01 | START | START | 95.6 | 1.2 | 0.3 | Clear, mildly yellow solution without visible particles |
| | | | | | 5° C. | 1 M | N/A | N/A | N/A | N/A |
| | | | | | 25° C. | 1 M | 90.4 | 3.2 | 2.8 | Clear, mildly yellow solution without visible particles |
| Vancomycin HCl + SBEβ-CD | 10% | 9.6% ethanol (V/V) in ultrapure water | 1:1.32 | 3.08 | START | START | 96.4 | 0.7 | 0.2 | Clear, colorless solution without visible particles |
| | | | | | 5° C. | 1 M | 96.2 | 0.8 | 0.2 | Clear, mildly yellow solution without visible particles |
| | | | | | 25° C. | 1 M | 92.1 | 2.6 | 1.9 | Clear, mildly yellow solution without visible particles |
| Vancomycin HCl + SBEβ-CD | 10% | 9.6% ethanol (V/V) in ultrapure water | 1:2 | 3.02 | START | START | 96.4 | 0.7 | 0.1 | Clear, mildly yellow solution without visible particles |
| | | | | | 5° C. | 1 M | 95.7 | 0.9 | 0.4 | Clear, mildly yellow solution without visible particles |
| | | | | | 25° C. | 1 M | 91.1 | 2.9 | 2.4 | Clear, mildly yellow solution without visible particles |
| Vancomycin HCl + SBEβ-CD | 5% | 9.6% ethanol (V/V) in ultrapure water | 1:2 | 3.14 | START | START | 96.4 | 0.6 | 0.2 | Clear, colorless solution without visible particles |
| | | | | | 5° C. | 1 M | 95.7 | 1.0 | 0.2 | Clear, colorless solution without visible particles |
| | | | | | 25° C. | 1 M | 90.6 | 3.0 | 2.7 | N/A |

TABLE 3

Accelerated stability data at 25° C./60% RH and long term stability data at 2-8° C. of Vancomycin liquid formulations containing SBEβ-CD and amino acids in a mixture of ethanol and ultrapure water

| Composition | Vancomycin conc. | Solvent | Molar ratio Van:CD:ALA:LYS | pH | Temperature | Time point | Purity % | DAMS % | CDP1 % | Appearance |
|---|---|---|---|---|---|---|---|---|---|---|
| Vancomycin HCl + SBEβ-CD + D-ALANINE + L-LYSINE | 10% | 9.6% ethanol (V/V) in ultrapure water | 1:2:1:1 | 2.95 | START | START | 96.4 | 0.7 | 0.1 | Clear, mildly yellow solution without visible particles |
| | | | | | 5° C. | 1 M | N/A | N/A | N/A | N/A |
| | | | | | 25° C. | 1 M | 93.6 | 1.8 | 1.6 | Clear, mildly yellow solution without visible particles |

TABLE 4

Accelerated stability data at 25° C./60% RH and long term stability data at 2-8° C. of Vancomycin liquid formulations containing SBEβ-CD in a mixture of different solvents

| Composition | Vancomycin conc. | Solvent | Molar ratio Van:CD | pH | Temperature | Time point | Purity % | DAMS % | CDP1 % | Appearance |
|---|---|---|---|---|---|---|---|---|---|---|
| Vancomycin HCl | 5% | Ultrapure water | / | 3.13 | START | START | 96.3 | 0.6 | 0.2 | Clear, colorless solution without visible particles |
| | | | | | 5° C. | 1 M | 95.8 | 1.3 | 0.2 | Clear, mildly yellow solution without visible particles |
| | | | | | 25° C. | 1 M | 86.6 | 4.5 | 6.0 | Clear, mildly yellow solution without visible particles |
| Vancomycin HCl + SBEβ-CD | 5% | Ultrapure water | 1:2 | 3.20 | START | START | 96.3 | 0.6 | 0.2 | Clear, colorless solution without visible particles |
| | | | | | 5° C. | 1 M | 95.8 | 1.0 | 0.2 | N/A |
| | | | | | 25° C. | 1 M | 90.2 | 3.0 | 3.3 | N/A |
| Vancomycin HCl + SBEβ-CD | 5% | 9.6% ethanol (V/V) in ultrapure water | 1:2 | 3.14 | START | START | 96.4 | 0.6 | 0.2 | Clear, colorless solution without visible particles |
| | | | | | 5° C. | 1 M | 95.7 | 1.0 | 0.2 | Clear, colorless solution without visible particles |
| | | | | | 25° C. | 1 M | 90.6 | 3.0 | 2.7 | N/A |
| Vancomycin HCl + SBEβ-CD | 5% | 28.8% (V/V) ethanol and 30% propylene glycol in ultrapure water | 1:2.2 | 3.20 | START | START | 96.3 | 0.6 | 0.2 | Clear, colorless solution without visible particles |
| | | | | | 5° C. | 1 M | 96.3 | 0.6 | 0.2 | Clear, mildly yellow, viscous solution without visible particles |
| | | | | | 25° C. | 1 M | 92.4 | 1.8 | 0.9 | Clear, mildly yellow, viscous solution without visible particles |
| Vancomycin HCl + SBEβ-CD | 5% | 55% PEG 400 in ultrapure water | 1:2.2 | 3.27 | START | START | 96.3 | 0.6 | 0.2 | Clear, colorless solution without visible particles |
| | | | | | 5° C. | 1 M | 95.9 | 0.5 | 0.2 | Clear, mildly yellow, viscous solution without visible particles |
| | | | | | 25° C. | 1 M | 93.9 | 1.5 | 0.5 | Clear, mildly yellow, viscous solution without visible particles |

TABLE 5

Accelerated stability data at 25° C./60% RH and long term stability data at 2-8° C. of Vancomycin liquid formulations containing SBEβ-CD and N-acetyl-D-Alanine in a mixture of different solvents

| Composition | Vancomycin conc. | Solvent | Molar ratio Van:CD:NADA | pH | Temperature | Time point | Purity % | DAMS % | CDP1 % | Appearance |
|---|---|---|---|---|---|---|---|---|---|---|
| Vancomycin HCl + SBEβ-CD + NADA | 5% | 9.6% ethanol (V/V) in ultrapure water | 1:2.2:2 | 3.11 | START | START | 96.4 | 0.6 | 0.2 | Clear, colorless solution without visible particles |
| | | | | | 5° C. | 1 M | 96.2 | 0.6 | 0.3 | Clear, colorless solution without visible particles |
| | | | | | 25° C. | 1 M | 94.7 | 1.1 | 0.6 | Clear, mildly yellow solution without visible particles |
| Vancomycin HCl + SBEβ-CD + NADA | 5% | 28.8% (V/V) ethanol and 30% propylene glycol in ultrapure water | 1:2.2:2 | 3.26 | START | START | 96.3 | 0.6 | 0.2 | Clear, colorless solution without visible particles |
| | | | | | 5° C. | 1 M | 96.2 | 0.6 | 0.2 | Clear, mildly yellow, mildly viscous solution without visible particles |
| | | | | | 25° C. | 1 M | 94.7 | 1.4 | 0.5 | Clear, mildly yellow, mildly viscous solution without visible particles |
| Vancomycin HCl + SBEβ-CD + NADA | 5% | 55% PEG 400 in ultrapure water | 1:2.2:2 | 3.31 | START | START | 96.2 | 0.6 | 0.2 | Clear, colorless solution without visible particles |
| | | | | | 5° C. | 1 M | 96.1 | 0.5 | 0.2 | Clear, mildly yellow, mildly viscous solution without visible particles |
| | | | | | 25° C. | 1 M | 95.1 | 1.1 | 0.4 | Clear, mildly yellow, mildly viscous solution without visible particles |

TABLE 6

Accelerated stability data at 25° C./60% RH and long term stability data at 2-8° C. of Vancomycin liquid formulations containing SBEβ-CD, N-acetyl-D-Alanine and amino acid in a mixture of different solvents

| Composition | Vancomycin conc. | Solvent | Molar ratio Van:CD:NADA:LYS | pH | Temperature | Time point | Purity % | DAMS % | CDP1 % | Appearance |
|---|---|---|---|---|---|---|---|---|---|---|
| Vancomycin HCl + SBEβ-CD + NADA + LYSINE | 5% | ultrapure water | 1:0.067:2:2 | 4.42 | START | START | 96.2 | 0.6 | 0.2 | Clear, mildly yellow solution without visible particles |
| | | | | | 5° C. | 1 M | N/A | N/A | N/A | Clear, mildly yellow solution without visible particles |
| | | | | | 25° C. | 1 M | 95.8 | 0.7 | 0.6 | Clear, mildly yellow solution without visible particles |
| Vancomycin HCl + SBEβ-CD + NADA + LYSINE | 5% | ultrapure water | 1:0.067:2:2 | 5.48 | START | START | 96.2 | 0.6 | 0.2 | Clear, mildly yellow solution without visible particles |
| | | | | | 5° C. | 1 M | N/A | N/A | N/A | Clear, mildly yellow solution without visible particles |
| | | | | | 25° C. | 1 M | 95.8 | 0.7 | 0.6 | Clear, mildly yellow solution without visible particles |
| Vancomycin HCl + SBEβ-CD + NADA + LYSINE | 5% | ultrapure water | 1:1.32:2:2 | 5.37 | START | START | 96.3 | 0.6 | 0.3 | Clear, colorless solution without visible particles |
| | | | | | 5° C. | 1 M | N/A | N/A | N/A | Clear, colorless solution without visible particles |
| | | | | | 25° C. | 1 M | 95.9 | 0.7 | 0.6 | Clear, colorless solution without visible particles |
| Vancomycin HCl + SBEβ-CD + NADA + LYSINE | 5% | ultrapure water | 1:2:2:2 | 5.38 | START | START | 96.3 | 0.6 | 0.2 | Clear, colorless solution without visible particles |
| | | | | | 5° C. | 1 M | N/A | N/A | N/A | Clear, colorless solution without visible particles |
| | | | | | 25° C. | 1 M | 95.6 | 0.7 | 0.5 | Clear, colorless solution without visible particles |
| Vancomycin HCl + SBEβ-CD + NADA + LYSINE | 5% | 28.8% (V/V) ethanol and 30% propylene glycol in ultrapure water | 1:2.2:2:2 | 5.49 | START | START | 96.2 | 0.6 | 0.2 | Clear, colorless solution without visible particles |
| | | | | | 5° C. | 1 M | 96.2 | 0.6 | 0.2 | Clear, mildly yellow, viscous solution without visible particles |
| | | | | | 25° C. | 1 M | 96.1 | 0.6 | 0.3 | Clear, mildly yellow, viscous solution without visible particles |
| Vancomycin HCl + SBEβ-CD + NADA + LYSINE | 5% | 10% PEG 400 in ultrapure water | 1:0.067:2:2 | 5.46 | START | START | 96.3 | 0.6 | 0.3 | Clear, colorless solution without visible particles |
| | | | | | 5° C. | 1 M | 96.2 | 0.6 | 0.3 | Clear, mildly yellow viscous solution without visible particles |
| | | | | | 25° C. | 1 M | 95.9 | 0.6 | 0.6 | Clear, mildly yellow viscous solution without visible particles |
| Vancomycin HCl + SBEβ-CD + NADA + LYSINE | 5% | 55% PEG 400 in ultrapure water | 1:2.2:2:2 | 5.53 | START | START | 96.2 | 0.6 | 0.2 | Clear, colorless solution without visible particles |
| | | | | | 5° C. | 1 M | 96.2 | 0.5 | 0.2 | Clear, mildly yellow, viscous solution without visible particles |
| | | | | | 25° C. | 1 M | 96.2 | 0.3 | 0.2 | Clear, mildly yellow, viscous solution without visible particles |

TABLE 7

Accelerated stability data at 25° C./60% RH and long term stability data at 2-8° C. of Vancomycin pre-mixed ready-to-use liquid formulations containing SBEβ-CD

| Composition | Vancomycin conc. | Solvent | Molar ratio Van:CD | pH | Temperature | Time point | Purity % | DAMS % | CDP1 % | Appearance |
|---|---|---|---|---|---|---|---|---|---|---|
| Vancomycin HCl | 0.5% | 0.9% NaCl | / | 3.00 | START | START | 96.0 | 0.7 | 0.3 | Clear, colorless solution without visible particles |
| | | | | | 5° C. | 1 M | 95.3 | 1.5 | 0.5 | Clear, colorless solution without visible particles |
| | | | | | 25° C. | 1 M | 80.5 | 4.9 | 11.0 | Clear, colorless solution without visible particles |
| Vancomycin HCl + SBEβ-CD | 0.5% | 0.9% NaCl | 1:20 | 3.30 | START | START | 95.1 | 0.2 | 0.1 | Clear, colorless solution without visible particles |
| | | | | | 5° C. | 1 M | 95.0 | 0.4 | 0.1 | Clear, colorless solution without visible particles |
| | | | | | 25° C. | 1 M | 84.9 | 30 | 57 | Clear, colorless solution without visible particles |

TABLE 7-continued

Accelerated stability data at 25° C./60% RH and long term stability data at 2-8° C. of Vancomycin pre-mixed ready-to-use liquid formulations containing SBEβ-CD

| Composition | Vancomycin conc. | Solvent | Molar ratio Van:CD | pH | Temperature | Time point | Purity % | DAMS % | CDP1 % | Appearance |
|---|---|---|---|---|---|---|---|---|---|---|
| Vancomycin HCl + SBEβ-CD | 0.5% | 0.9% NaCl | 1:20 | 5.39 | START | START | 95.1 | 0.2 | 0.1 | Clear, colorless solution without visible particles |
| | | | | | 5° C. | 1 M | 94.9 | 0.3 | 0.3 | Clear, colorless solution without visible particles |
| | | | | | 25° C. | 1 M | 88.9 | 1.4 | 50 | Clear, colorless solution without visible particles |
| Vancomycin HCl + SBEβ-CD | 0.5% | 9.6% ethanol (V/V) in 0.9% NaCl | 1:20 | 3.19 | START | START | 95.1 | 0.2 | 0.1 | Clear, colorless solution without visible particles |
| | | | | | 5° C. | 1 M | 95.1 | 0.2 | 0.1 | Clear, colorless solution without visible particles |
| | | | | | 25° C. | 1 M | 86.4 | 2.9 | 4.0 | Clear, colorless solution without visible particles |
| Vancomycin HCl + SBEβ-CD | 0.5% | 9.6% ethanol (V/V) in 0.9% NaCl | 1:20 | 5.20 | START | START | 95.1 | 0.2 | 0.1 | Clear, colorless solution without visible particles |
| | | | | | 5° C. | 1 M | 95.1 | 0.2 | 0.1 | Clear, colorless solution without visible particles |
| | | | | | 25° C. | 1 M | 89.7 | 1.1 | 3.9 | Clear, colorless solution without visible particles |
| Vancomycin HCl + SBEβ-CD | 0.5% | 9.6% ethanol (V/V) in 0.9% NaCl | 1:1.32 | 3.03 | START | START | 96.3 | 0.7 | 0.3 | Clear, colorless solution without visible particles |
| | | | | | 5° C. | 1 M | 95.5 | 1.2 | 0.3 | Clear, colorless solution without visible particles |
| | | | | | 25° C. | 1 M | 85.2 | 4.4 | 6.5 | Clear, colorless solution without visible particles |
| Vancomycin HCl + SBEβ-CD | 0.5% | 9.6% ethanol (V/V) in 0.9% NaCl | 1:3.3 | 2.99 | START | START | 96.2 | 0.7 | 0.2 | Clear, mildly yellow solution without visible particles |
| | | | | | 5° C. | 1 M | 95.8 | 1.2 | 0.4 | Clear, colorless solution without visible particles |
| | | | | | 25° C. | 1 M | 84.0 | 4.3 | 7.5 | Clear, colorless solution without visible particles |
| Vancomycin HCl + SBEβ-CD | 0.5% | 9.6% ethanol (V/V) in 0.9% NaCl | 1:6.7 | 3.02 | START | START | 96.3 | 0.7 | 0.1 | Clear, mildly yellow solution without visible particles |
| | | | | | 5° C. | 1 M | 95.9 | 1.2 | 0.3 | Clear, colorless solution without visible particles |
| | | | | | 25° C. | 1 M | 86.4 | 4.0 | 5.5 | Clear, colorless solution without visible particles |

TABLE 8

Accelerated stability data at 25° C. /60% RH and long term stability data at 2-8° C. of Vancomycin pre-mixed ready-to-use liquid formulations containing SBEβ-CD, N-acetyl-D-Alanine and amino acid in a mixture of different solvents

| Composition | Vancomycin conc. | Solvent | Molar ratio Van:CD:NADA:LYS | pH | Temperature | Time point | Purity % | DAMS % | CDP1 % | Appearance |
|---|---|---|---|---|---|---|---|---|---|---|
| Vancomycin HCl + SBEβ-CD + NADA + LYSINE | 0.5% | 0.9% NaCl | 1:0.67:20:20 | 5.48 | START | START | 96.4 | 0.6 | 0.3 | Clear, colorless solution without visible particles |
| | | | | | 5° C. | 1 M | 96.4 | 0.6 | 0.3 | Clear, colorless solution without visible particles |
| | | | | | 25° C. | 1 M | 96.0 | 0.6 | 0.6 | Clear, colorless solution without visible particles |
| Vancomycin HCl + SBEβ-CD + NADA + LYSINE | 0.5% | 0.9% NaCl | 1:20:20:20 | 5.38 | START | START | 96.2 | 0.7 | 0.2 | Clear, colorless solution without visible particles |
| | | | | | 5° C. | 1 M | N/A | N/A | N/A | Clear, colorless solution without visible particles |
| | | | | | 25° C. | 1 M | 95.7 | 0.7 | 0.5 | N/A |
| Vancomycin HCl + SBEβ-CD + NADA + LYSINE | 0.5% | 0.9% NaCl | 1:0.67:30:20 | 5.43 | START | START | 96.4 | 0.6 | 0.3 | Clear, colorless solution without visible particles |
| | | | | | 5° C. | 1 M | 96.4 | 0.6 | 0.2 | Clear, colorless solution without visible particles |
| | | | | | 25° C. | 1 M | 96.0 | 0.6 | 0.6 | Clear, colorless solution without visible particles |
| Vancomycin HCl + SBEβ-CD + NADA + LYSINE | 0.5% | 0.9% NaCl | 1:6.7:30:20 | 5.50 | START | START | 96.3 | 0.6 | 0.2 | Clear, colorless solution without visible particles |
| | | | | | 5° C. | 1 M | 96.4 | 0.6 | 0.2 | Clear, colorless solution without visible particles |
| | | | | | 25° C. | 1 M | 95.9 | 0.6 | 0.4 | Clear, colorless solution without visible particles |

TABLE 8-continued

Accelerated stability data at 25° C. /60% RH and long term stability data at 2-8° C. of Vancomycin pre-mixed ready-to-use liquid formulations containing SBEβ-CD, N-acetyl-D-Alanine and amino acid in a mixture of different solvents

| Composition | Vancomycin conc. | Solvent | Molar ratio Van:CD:NADA:LYS | pH | Temperature | Time point | Purity % | DAMS % | CDP1 % | Appearance |
|---|---|---|---|---|---|---|---|---|---|---|
| Vancomycin HCl + SBEβ-CD + NADA + LYSINE | 0.5% | 5.5% PEG 400 in 0.9% NaCl | 1:6.7:20:20 | 5.45 | START | START | 96.2 | 0.6 | 0.3 | Clear, colorless solution without visible particles |
| | | | | | 5° C. | 1 M | 96.3 | 0.6 | 0.2 | Clear, colorless solution without visible particles |
| | | | | | 25° C. | 1 M | 95.8 | 0.6 | 0.4 | Clear, colorless solution without visible particles |
| Vancomycin HCl + SBEβ-CD + NADA + LYSINE | 0.5% | 5.5% PEG 400 in 0.9% NaCl | 1:6.7:30:20 | 5.46 | START | START | 96.3 | 0.6 | 0.2 | Clear, colorless solution without visible particles |
| | | | | | 5° C. | 1 M | 96.2 | 0.6 | 0.2 | Clear, colorless solution without visible particles |
| | | | | | 25° C. | 1 M | 96.0 | 0.6 | 0.4 | Clear, colorless solution without visible particles |
| Vancomycin HCl + SBEβ-CD + NADA + LYSINE | 0.5% | 5% dextrose | 1:20:20:20 | 5.49 | START | START | 96.2 | 0.7 | 0.2 | Clear, colorless solution without visible particles |
| | | | | | 5° C. | 1 M | N/A | N/A | N/A | Clear, colorless solution without visible particles |
| | | | | | 25° C. | 1 M | 95.6 | 0.5 | 0.6 | Clear, colorless solution without visible particles |
| Vancomycin HCl + SBEβ-CD + NADA + LYSINE | 0.5% | 5.5% PEG 400 in 5% dextrose | 1:6.7:20:20 | 5.47 | START | START | 96.2 | 0.6 | 0.2 | Clear, colorless solution without visible particles |
| | | | | | 5° C. | 1 M | 96.3 | 0.6 | 0.2 | Clear, mildly yellow, mildly viscous solution without visible particles |
| | | | | | 25° C. | 1 M | 95.8 | 0.5 | 0.4 | Clear, mildly yellow, mildly viscous solution without visible particles |

TABLE 9

Stability data at 30° C./65% RH of Vancomycin liquid formulations containing SBEβ-CD

| Composition | Vancomycin conc. | Solvent | Molar ratio Van:CD:NADA:LYS | pH | Temperature | Time point | Purity % | DAMS % | CDP1 % | Appearance |
|---|---|---|---|---|---|---|---|---|---|---|
| Vancomycin HCl + SBEβ-CD | 10% | 9.6% ethanol (V/V) in ultrapure water | 1:1 | 3.01 | START | START | 95.6 | 1.2 | 0.3 | Clear, mildly yellow solution without visible particles |
| | | | | | 30° C. | 1 M | 84.5 | 4.5 | 6.1 | Clear, mildly yellow solution without visible particles |
| Vancomycin HCl + SBEβ-CD | 10% | 9.6% ethanol (V/V) in ultrapure water | 1:1.32 | 3.08 | START | START | 96.4 | 0.7 | 0.2 | Clear, colorless solution without visible particles |
| | | | | | 30° C. | 1 M | 87.1 | 3.8 | 4.4 | Clear, mildly yellow solution without visible particles |
| Vancomycin HCl + SBEβ-CD | 10% | 9.6% ethanol (V/V) in ultrapure water | 1:2 | 3.02 | START | START | 96.4 | 0.7 | 0.1 | Clear, mildly yellow solution without visible particles |
| | | | | | 30° C. | 1 M | 86.0 | 4.1 | 5.2 | Clear, mildly yellow solution without visible particles |
| Vancomycin HCl | 0.5% | 0.9% NaCl | / | 3.00 | START | START | 96.0 | 0.7 | 0.3 | Clear, colorless solution without visible particles |
| | | | | | 30° C. | 1 M | 68.7 | 5.0 | 21.6 | Clear, colorless solution without visible particles |
| Vancomycin HCl + SBEβ-CD | 0.5% | 9.6% ethanol (V/V) in 0.9% NaCl | 1:1.32 | 3.03 | START | START | 96.3 | 0.7 | 0.3 | Clear, colorless solution without visible particles |
| | | | | | 30° C. | 1 M | 75.9 | 4.8 | 13.7 | Clear, colorless solution without visible particles |
| Vancomycin HCl + SBEβ-CD | 0.5% | 9.6% ethanol (V/V) in 0.9% NaCl | 1:3.3 | 2.99 | START | START | 96.2 | 0.7 | 0.2 | Clear, mildly yellow solution without visible particles |
| | | | | | 30° C. | 1 M | 78.9 | 4.8 | 11.2 | Clear, colorless solution without visible particles |
| Vancomycin HCl + SBEβ-CD | 0.5% | 9.6% ethanol (V/V) in 0.9% NaCl | 1:3.3 | 2.99 | START | START | 96.3 | 0.7 | 0.1 | Clear, mildly yellow solution without visible particles |
| | | | | | 30° C. | 1 M | 77.5 | 4.7 | 11.5 | Clear, colorless solution without visible particles |
| Vancomycin HCl + SBEβ-CD + D- | 10% | 9.6% ethanol (V/V) in | 1:2:1:1 | 2.95 | START | START | 96.4 | 0.7 | 0.1 | Clear, mildly yellow solution without visible particles |
| | | | | | 30° C. | 1 M | 92.0 | 2.2 | 2.3 | Clear, yellow solution |

TABLE 9-continued

Stability data at 30° C./65% RH of Vancomycin liquid formulations containing SBEβ-CD

| Composition | Vancomycin conc. | Solvent | Molar ratio Van:CD:NADA:LYS | pH | Temperature | Time point | Purity % | DAMS % | CDP1 % | Appearance |
|---|---|---|---|---|---|---|---|---|---|---|
| ALANINE + L-LYSINE | | ultrapure water | | | | | | | | without visible particles |
| Vancomycin HCl + SBEβ-CD + NADA + LYSINE | 5% | ultrapure water | 1:0.067:2:2 | 4.42 | START | START | 96.2 | 0.6 | 0.2 | Clear, mildly yellow solution without visible particles |
| | | | | | 30° C. | 1 M | 95.2 | 0.8 | 1.2 | Clear, mildly yellow solution without visible particles |
| Vancomycin HCl + SBEβ-CD + NADA + LYSINE | 5% | ultrapure water | 1:0.067:2:2 | 5.48 | START | START | 96.2 | 0.6 | 0.2 | Clear, mildly yellow solution without visible particles |
| | | | | | 30° C. | 1 M | 95.2 | 0.7 | 1.3 | Clear, mildly yellow solution without visible particles |
| Vancomycin HCl + SBEβ-CD + NADA + LYSINE | 5% | ultrapure water | 1:1.32:2:2 | 5.37 | START | START | 96.3 | 0.6 | 0.3 | Clear, colorless solution without visible particles |
| | | | | | 30° C. | 1 M | 95.4 | 0.7 | 1.0 | Clear, colorless solution without visible particles |
| | | | | | 30° C. | 2 M | 94.4 | 0.7 | 2.1 | Clear, mildly yellow solution without visible particles |
| | | | | | 30° C. | 3 M | 93.1 | 0.7 | 3.0 | Clear, mildly yellow solution without visible particles |
| Vancomycin HCl + SBEβ-CD + NADA + LYSINE | 5% | ultrapure water | 1:2:2:2 | 5.38 | START | START | 96.3 | 0.6 | 0.2 | Clear, colorless solution without visible particles |
| | | | | | 30° C. | 1 M | 95.1 | 0.7 | 0.8 | Clear, colorless solution without visible particles |
| | | | | | 30° C. | 2 M | 94.5 | 0.6 | 1.7 | Clear, mildly yellow solution without visible particles |
| | | | | | 30° C. | 3 M | 93.4 | 0.7 | 2.7 | Clear, mildly yellow solution without visible particles |
| Vancomycin HCl + SBEβ-CD + NADA + LYSINE | 0.5% | 0.9% NaCl | 1:6.7:20:20 | 5.00 | START | START | 94.8 | 0.1 | 0.1 | Clear, colorless solution without visible particles |
| | | | | | 30° C. | 1 M | N/A | N/A | N/A | Clear, colorless solution without visible particles |
| | | | | | 30° C. | 2 M | 92.8 | 0.1 | 2.1 | Clear, colorless solution without visible particles |
| | | | | | 30° C. | 3 M | 91.7 | 0.3 | 2.7 | Clear, colorless solution without visible particles |
| Vancomycin HCl + SBEβ-CD + NADA + LYSINE | 0.5% | 0.9% NaCl | 1:20:20:20 | 5.38 | START | START | 96.2 | 0.7 | 0.2 | Clear, colorless solution without visible particles |
| | | | | | 30° C. | 1 M | 95.2 | 0.7 | 0.9 | Clear, colorless solution without visible particles |
| | | | | | 30° C. | 2 M | 94.2 | 0.7 | 1.9 | Clear, colorless solution with visible particles |
| | | | | | 30° C. | 3 M | 93.2 | 0.7 | 2.6 | Clear, mildly yellow solution without visible particles |
| Vancomycin HCl + SBEβ-CD + NADA + LYSINE | 0.5% | 5% dextrose | 1:20:20:20 | 5.49 | START | START | 96.2 | 0.7 | 0.2 | Clear, colorless solution without visible particles |
| | | | | | 30° C. | 1 M | 94.9 | 0.5 | 1.0 | Clear, mildly yellow solution without visible particles |
| | | | | | 30° C. | 2 M | 93.5 | 0.7 | 2.0 | Clear, mildly yellow solution without visible particles |
| | | | | | 30° C. | 3 M | 92.2 | 0.6 | 3.0 | Clear, mildly yellow solution without visible particles |

TABLE 10

Stability data of Vancomycin liquid formulations containing SBEβ-CD in different packaging materials

| Composition | Vancomycin conc. | Solvent | Molar ratio Van:CD:NADA:LYS | pH | Temperature | Time point | Purity % | DAMS % | CDP1 % | Packaging | Appearance |
|---|---|---|---|---|---|---|---|---|---|---|---|
| Vancomycin HCl + SBEβ-CD + NADA + LYSINE | 0.5% | 0.9% NaCl | 1:0.67:30:20 | 5.0 | START | START | 96.2 | 0.59 | 0.3 | vials with bromobutyl Fluro Tec stoppers - upright position | The solution is essentially free from particles of foreign matter that can be observed on visual inspection |
| | | | | | 5° C. | 1 M 11 D | 96.2 | 0.58 | 0.2 | | The solution is essentially free from particles of foreign |

TABLE 10-continued

Stability data of Vancomycin liquid formulations containing SBEβ-CD in different packaging materials

| Composition | Vanco-mycin conc. | Solvent | Molar ratio Van:CD:NADA:LYS | pH | Tem-perature | Time point | Purity % | DAMS % | CDP1 % | Packaging | Appearance |
|---|---|---|---|---|---|---|---|---|---|---|---|
| | | | | | 25° C. | 1 M 11 D | 95.8 | 0.60 | 0.6 | | matter that can be observed on visual inspection The solution is essentially free from particles of foreign matter that can be observed on visual inspection |
| | | | | | 30° C. | 1 M 11 D | 95.1 | 0.63 | 1.3 | | The solution is essentially free from particles of foreign matter that can be observed on visual inspection |
| Vancomycin HCl + SBEβ-CD + NADA + LYSINE | 0.5% | 0.9% NaCl | 1:0.67:30:20 | 5.0 | START | START | 96.2 | 0.59 | 0.3 | Blow/Fill/Seal vials | The solution is essentially free from particles of foreign matter that can be observed on visual inspection |
| | | | | | 5° C. | 1 M 11 D | 96.2 | 0.58 | 0.2 | | The solution is essentially free from particles of foreign matter that can be observed on visual inspection |
| | | | | | 25° C. | 1 M 11 D | 95.8 | 0.60 | 0.6 | | The solution is essentially free from particles of foreign matter that can be observed on visual inspection |
| | | | | | 30° C. | 1 M 11 D | 95.1 | 0.63 | 1.2 | | The solution is essentially free from particles of foreign matter that can be observed on visual inspection |
| Vancomycin HCl + SBEβ-CD + NADA + LYSINE | 0.5% | 0.9% NaCl | 1:0.67:30:20 | 5.0 | START | START | 96.3 | 0.58 | 0.3 | Technoflex PE IV bags | The solution is essentially free from particles of foreign matter that can be observed on visual inspection |
| | | | | | 5° C. | 1 M 11 D | 96.2 | 0.57 | 0.3 | | The solution is essentially free from particles of foreign matter that can be observed on visual inspection |
| | | | | | 25° C./ 60% RH | 1 M 11 D | 95.9 | 0.60 | 0.5 | | The solution is essentially free from particles of foreign matter that can be observed on visual inspection |
| | | | | | 30° C./ 65% RH | 1 M 11 D | 95.4 | 0.61 | 1.1 | | The solution is essentially free from particles of foreign matter that can be observed on visual inspection |
| Vancomycin HCl + SBEβ-CD + NADA + LYSINE | 0.5% | 0.9% NaCl | 1:0.67:30:20 | 5.0 | START | START | 96.3 | 0.59 | 0.3 | Technoflex PP IV bags | The solution is essentially free from particles of foreign matter that can be observed on visual inspection |
| | | | | | 5° C. | 1 M 11 D | 96.3 | 0.58 | 0.2 | | The solution is essentially free from particles of foreign matter that can be |

TABLE 10-continued

Stability data of Vancomycin liquid formulations containing SBEβ-CD in different packaging materials

| Composition | Vancomycin conc. | Solvent | Molar ratio Van:CD:NADA:LYS | pH | Temperature | Time point | Purity % | DAMS % | CDP1 % | Packaging | Appearance |
|---|---|---|---|---|---|---|---|---|---|---|---|
| | | | | | 25° C./ 60% RH | 1 M 11 D | 95.9 | 0.60 | 0.6 | | observed on visual inspection The solution is essentially free from particles of foreign matter that can be observed on visual inspection |
| | | | | | 30° C./ 65% RH | 1 M 11 D | 95.4 | 0.61 | 1.0 | | The solution is essentially free from particles of foreign matter that can be observed on visual inspection |
| Vancomycin HCl + SBEβ-CD + NADA + LYSINE | 0.5% | 0.9% NaCl | 1:0.67:30:20 | 5.0 | START | START | 96.3 | 0.58 | 0.3 | Renolit PE IV bags | The solution is essentially free from particles of foreign matter that can be observed on visual inspection |
| | | | | | 5° C. | 1 M | 96.2 | 0.59 | 0.3 | | The solution is essentially free from particles of foreign matter that can be observed on visual inspection |
| | | | | | 25° C./ 60% RH | 1 M | 95.9 | 0.58 | 0.5 | | The solution is essentially free from particles of foreign matter that can be observed on visual inspection |
| | | | | | 30° C./ 65% RH | 1 M | 95.3 | 0.59 | 0.9 | | The solution is essentially free from particles of foreign matter that can be observed on visual inspection |
| Vancomycin HCl + SBEβ-CD + NADA + LYSINE | 0.5% | 0.9% NaCl | 1:0.67:30:20 | 5.0 | START | START | 96.1 | 0.61 | 0.2 | Polycine PP IV bags | The solution is essentially free from particles of foreign matter that can be observed on visual inspection |
| | | | | | 5° C. | 1 M | 96.0 | 0.63 | 0.2 | | The solution is essentially free from particles of foreign matter that can be observed on visual inspection |
| | | | | | 25° C./ 60% RH | 1 M | 95.7 | 0.60 | 0.5 | | The solution is essentially free from particles of foreign matter that can be observed on visual inspection |
| | | | | | 30° C./ 65% RH | 1 M | 95.1 | 0.61 | 0.9 | | The solution is essentially free from particles of foreign matter that can be observed on visual inspection |
| Vancomycin HCl + SBEβ-CD + NADA + LYSINE | 0.5% | 0.9% NaCl | 1:0.67:30:20 | 5.1 | START | START | 96.1 | 0.62 | 0.2 | Sealed Air PE IV bags | The solution is essentially free from particles of foreign matter that can be observed on visual inspection |
| | | | | | 5° C. | 1 M | 96.0 | 0.63 | 0.2 | | The solution is essentially free from particles of foreign |

TABLE 10-continued

Stability data of Vancomycin liquid formulations containing SBEβ-CD in different packaging materials

| Composition | Vancomycin conc. | Solvent | Molar ratio Van:CD:NADA:LYS | pH | Temperature | Time point | Purity % | DAMS % | CDP1 % | Packaging | Appearance |
|---|---|---|---|---|---|---|---|---|---|---|---|
| | | | | | 25° C./40% RH | 1 M | 95.7 | 0.61 | 0.5 | | matter that can be observed on visual inspection The solution is essentially free from particles of foreign matter that can be observed on visual inspection |
| | | | | | 30° C./65% RH | 1 M | 95.2 | 0.61 | 0.8 | | The solution is essentially free from particles of foreign matter that can be observed on visual inspection |

TABLE 11

Stability data of Vancomycin liquid formulations in different packaging materials

| Composition | Vancomycin conc. | Solvent | Molar ratio | pH | Temperature | Time point | Purity % | DAMS % | CDP1 % | Packaging | Appearance |
|---|---|---|---|---|---|---|---|---|---|---|---|
| Vancomycin HCl + LYSINE + NADA | 0.5% | 0.9% NaCl | 1:20:30 | 5.0 | START | START | 96.2 | 0.59 | 0.3 | vials with bromobutyl Fluro Tec stoppers - upright position | The solution is essentially free from particles of foreign matter that can be observed on visual inspection |
| | | | | | 5° C. | 1 M | 96.3 | 0.57 | 0.2 | | The solution is essentially free from particles of foreign matter that can be observed on visual inspection. |
| | | | | | 25° C./60% RH | 1 M | 95.9 | 0.62 | 0.5 | | The solution is essentially free from particles of foreign matter that can be observed on visual inspection |
| | | | | | 30° C./65% RH | 1 M | 95.7 | 0.63 | 0.9 | | The solution is essentially free from particles of foreign matter that can be observed on visual inspection |
| Vancomycin HCl + LYSINE + NADA | 0.5% | 0.9% NaCl | 1:20:30 | 5.0 | START | START | 96.2 | 0.59 | 0.3 | Blow/Fill/Seal vials | The solution is essentially free from particles of foreign matter that can be observed on visual inspection |
| | | | | | 5° C. | 1 M | 96.2 | 0.58 | 0.2 | | The solution is essentially free from particles of foreign matter that can be observed on visual inspection |
| | | | | | 25° C./60% RH | 1 M | 96.0 | 0.62 | 0.5 | | The solution is essentially free from particles of foreign matter that can be observed on visual inspection |
| | | | | | 30° C./65% RH | 1 M | 95.6 | 0.63 | 0.9 | | The solution is essentially free from particles of foreign matter that can be |

TABLE 11-continued

Stability data of Vancomycin liquid formulations in different packaging materials

| Composition | Vancomycin conc. | Solvent | Molar ratio | pH | Temperature | Time point | Purity % | DAMS % | CDP1 % | Packaging | Appearance |
|---|---|---|---|---|---|---|---|---|---|---|---|
| Vancomycin HCl + LYSINE + NADA | 0.5% | 0.9% NaCl | 1:20:30 | 5.0 | START | START | 96.2 | 0.58 | 0.2 | Technoflex PE IV bags | The solution is essentially free from particles of foreign matter that can be observed on visual inspection |
| | | | | | 5° C. | 3 W | 96.2 | 0.59 | 0.3 | | The solution is essentially free from particles of foreign matter that can be observed on visual inspection |
| | | | | | 25° C./60% RH | 3 W | 96.0 | 0.63 | 0.4 | | The solution is essentially free from particles of foreign matter that can be observed on visual inspection |
| | | | | | 30° C./65% RH | 3 W | 95.8 | 0.63 | 0.7 | | The solution is essentially free from particles of foreign matter that can be observed on visual inspection |
| Vancomycin HCl + LYSINE + NADA | 0.5% | 0.9% NaCl | 1:20:30 | 5.0 | START | START | 96.3 | 0.57 | 0.3 | Technoflex PP IV bags | The solution is essentially free from particles of foreign matter that can be observed on visual inspection |
| | | | | | 5° C. | 1 M | 96.2 | 0.59 | 0.3 | | The solution is essentially free from particles of foreign matter that can be observed on visual inspection |
| | | | | | 25° C./60% RH | 1 M | 96.0 | 0.62 | 0.5 | | The solution is essentially free from particles of foreign matter that can be observed on visual inspection |
| | | | | | 30° C./65% RH | 1 M | 95.8 | 0.63 | 0.7 | | The solution is essentially free from particles of foreign matter that can be observed on visual inspection |
| Vancomycin HCl + LYSINE + NADA | 0.5% | 0.9% NaCl | 1:20:30 | 5.0 | START | START | 96.1 | 0.58 | 0.3 | Renolit PE IV bags | The solution is essentially free from particles of foreign matter that can be observed on visual inspection |
| | | | | | 5° C. | 1 M | 96.1 | 0.58 | 0.3 | | The solution is essentially free from particles of foreign matter that can be observed on visual inspection |
| | | | | | 25° C./60% RH | 1 M | 95.7 | 0.57 | 0.5 | | The solution is essentially free from particles of foreign matter that can be observed on visual inspection |
| | | | | | 30° C./65% RH | 1 M | 95.4 | 0.58 | 0.9 | | The solution is essentially free from particles of foreign matter that can be observed on visual inspection |

TABLE 11-continued

Stability data of Vancomycin liquid formulations in different packaging materials

| Composition | Vancomycin conc. | Solvent | Molar ratio | pH | Temperature | Time point | Purity % | DAMS % | CDP1 % | Packaging | Appearance |
|---|---|---|---|---|---|---|---|---|---|---|---|
| Vancomycin HCl + LYSINE + NADA | 0.5% | 0.9% NaCl | 1:20:30 | 5.2 | START | START | 96.2 | 0.58 | 0.3 | Polycine PP IV bags | The solution is essentially free from particles of foreign matter that can be observed on visual inspection |
| | | | | | 5° C. | 1 M | 96.1 | 0.58 | 0.3 | | The solution is essentially free from particles of foreign matter that can be observed on visual inspection |
| | | | | | 25° C./60% RH | 1 M | 95.8 | 0.58 | 0.6 | | The solution is essentially free from particles of foreign matter that can be observed on visual inspection |
| | | | | | 30° C./65% RH | 1 M | 95.5 | 0.58 | 0.9 | | The solution is essentially free from particles of foreign matter that can be observed on visual inspection |
| Vancomycin HCl + LYSINE + NADA | 0.5% | 0.9% NaCl | 1:20:30 | 5.0 | START | START | 96.2 | 0.58 | 0.3 | Sealed Air PE IV bags | The solution is essentially free from particles of foreign matter that can be observed on visual inspection |
| | | | | | 5° C. | 1 M | 96.2 | 0.58 | 0.3 | | The solution is essentially free from particles of foreign matter that can be observed on visual inspection |
| | | | | | 25° C./40% RH | 1 M | 95.9 | 0.55 | 0.6 | | The solution is essentially free from particles of foreign matter that can be observed on visual inspection |
| | | | | | 30° C./65% RH | 1 M | 95.6 | 0.55 | 0.9 | | The solution is essentially free from particles of foreign matter that can be observed on visual inspection |
| Vancomycin HCl + LYSINE + NADA | 0.5% | 0.9% NaCl | 1:20:30 | 5.0 | START | START | 96.3 | 0.59 | 0.3 | Holopack Blow/Fill/Seal Purell RP270G, medium modified copolymer | The solution is essentially free from particles of foreign matter that can be observed on visual inspection |
| | | | | | 5° C. | 1 M | 96.3 | 0.55 | 0.3 | | The solution is essentially free from particles of foreign matter that can be observed on visual inspection |
| | | | | | 25° C./40% RH | 1 M | 95.9 | 0.54 | 0.6 | | The solution is essentially free from particles of foreign matter that can be observed on visual inspection |
| | | | | | 30° C./65% RH | 1 M | 95.5 | 0.54 | 1.0 | | The solution is essentially free from particles of foreign matter that can be observed on visual inspection |

TABLE 11-continued

Stability data of Vancomycin liquid formulations in different packaging materials

| Composition | Vancomycin conc. | Solvent | Molar ratio | pH | Temperature | Time point | Purity % | DAMS % | CDP1 % | Packaging | Appearance |
|---|---|---|---|---|---|---|---|---|---|---|---|
| Vancomycin HCl + LYSINE + NADA | 0.5% | 0.9% NaCl | 1:20:30 | 5.0 | START | START | 96.3 | 0.59 | 0.3 | Holopack Blow/Fill/Seal Purell PE 3020D, low density polyethylene | The solution is essentially free from particles of foreign matter that can be observed on visual inspection |
| | | | | | 5° C. | 1 M | 96.3 | 0.55 | 0.3 | | The solution is essentially free from particles of foreign matter that can be observed on visual inspection |
| | | | | | 25° C./40% RH | 1 M | 96.0 | 0.53 | 0.6 | | The solution is essentially free from particles of foreign matter that can be observed on visual inspection |
| | | | | | 30° C./65% RH | 1 M | 95.5 | 0.54 | 1.1 | | The solution is essentially free from particles of foreign matter that can be observed on visual inspection |
| Vancomycin HCl + LYSINE + NADA | 0.5% | 0.9% NaCl | 1:20:30 | 5.0 | START | START | 96.3 | 0.59 | 0.3 | Holopack Blow/Fill/Seal Purell PE 3040D, low density polyethylene | The solution is essentially free from particles of foreign matter that can be observed on visual inspection |
| | | | | | 5° C. | 1 M | 96.2 | 0.56 | 0.3 | | The solution is essentially free from particles of foreign matter that can be observed on visual inspection |
| | | | | | 25° C./40% RH | 1 M | 96.0 | 0.53 | 0.6 | | The solution is essentially free from particles of foreign matter that can be observed on visual inspection |
| | | | | | 30° C./65% RH | 1 M | 95.3 | 0.56 | 1.0 | | The solution is essentially free from particles of foreign matter that can be observed on visual inspection |
| Vancomycin HCl + LYSINE + NADA | 0.5% | 1.8% PEG 400 + 98.2% 0.9% NaCl | 1:20:30 | 5.0 | START | START | 96.2 | 0.58 | 0.3 | Technoflex PP IV bags | The solution is essentially free from particles of foreign matter that can be observed on visual inspection |
| | | | | | 5° C. | 1 M 6 D | NA | NA | NA | | NA |
| | | | | | 25° C./60% RH | 1 M 6 D | 95.8 | 0.52 | 0.6 | | The solution is essentially free from particles of foreign matter that can be observed on visual inspection |
| | | | | | 30° C./65% RH | 1 M 6 D | 95.5 | 0.53 | 1.0 | | The solution is essentially free from particles of foreign matter that can be observed on visual inspection |
| Vancomycin HCl + LYSINE + NADA | 0.5% | 1.8% PEG 400 + 98.2% 0.9% NaCl | 1:20:30 | 5.0 | START | START | 96.2 | 0.58 | 0.3 | Technoflex PE IV bags | The solution is essentially free from particles of foreign matter that can be observed on visual inspection |

TABLE 11-continued

Stability data of Vancomycin liquid formulations in different packaging materials

| Composition | Vancomycin conc. | Solvent | Molar ratio | pH | Temperature | Time point | Purity % | DAMS % | CDP1 % | Packaging | Appearance |
|---|---|---|---|---|---|---|---|---|---|---|---|
| | | | | | 5° C. | 1 M 11 D | NA | NA | NA | | NA |
| | | | | | 25° C./60%RH | 1 M 11 D | 95.9 | 0.52 | 0.6 | | The solution is essentially free from particles of foreign matter that can be observed on visual inspection |
| | | | | | 30° C./65% RH | 1 M 11 D | 95.4 | 0.54 | 1.1 | | The solution is essentially free from particles of foreign matter that can be observed on visual inspection |
| Vancomycin HCl + LYSINE + NADA | 0.5% | 1.8% PEG 400 + 98.2% 0.9% NaCl | 1:20:30 | 5.0 | START | START | 96.2 | 0.57 | 0.3 | vials with bromobutyl Fluro Tec stoppers - inverted | The solution is essentially free from particles of foreign matter that can be observed on visual inspection |
| | | | | | 5° C. | 1 M 7 D | 96.1 | 0.50 | 0.3 | | The solution is essentially free from particles of foreign matter that can be observed on visual inspection |
| | | | | | 25° C./60% RH | 1 M 7 D | 95.9 | 0.52 | 0.6 | | The solution is essentially free from particles of foreign matter that can be observed on visual inspection |
| | | | | | 30° C./65% RH | 1 M 7 D | 95.5 | 0.53 | 1.0 | | The solution is essentially free from particles of foreign matter that can be observed on visual inspection |
| Vancomycin HCl + LYSINE + NADA | 0.5% | 1.8% PEG 400 + 98.2% 0.9% NaCl | 1:20:30 | 5.0 | START | START | 96.2 | 0.57 | 0.3 | BFS vials | The solution is essentially free from particles of foreign matter that can be observed on visual inspection |
| | | | | | 5° C. | 1 M 7 D | 96.1 | 0.50 | 0.3 | | The solution is essentially free from particles of foreign matter that can be observed on visual inspection |
| | | | | | 25° C./60% RH | 1 M 7 D | 95.9 | 0.52 | 0.6 | | The solution is essentially free from particles of foreign matter that can be observed on visual inspection |
| | | | | | 30° C./65% RH | 1 M 7 D | 95.5 | 0.53 | 1.0 | | The solution is essentially free from particles of foreign matter that can be observed on visual inspection |
| Vancomycin HCl + LYSINE + NADA | 0.5% | 1.8% PEG 400 + 98.2% 0.9% NaCl | 1:20:30 | 5.0 | START | START | 96.3 | 0.55 | 0.3 | Sealed Air PE IV bags | The solution is essentially free from particles of foreign matter that can be observed on visual inspection |
| | | | | | 5° C. | 1 M | 96.2 | 0.53 | 0.3 | | The solution is essentially free from particles of foreign matter that can be observed on visual inspection |

TABLE 11-continued

Stability data of Vancomycin liquid formulations in different packaging materials

| Composition | Vancomycin conc. | Solvent | Molar ratio | pH | Temperature | Time point | Purity % | DAMS % | CDP1 % | Packaging | Appearance |
|---|---|---|---|---|---|---|---|---|---|---|---|
| | | | | | 25° C./40% RH | 1 M | 95.9 | 0.51 | 0.5 | | The solution is essentially free from particles of foreign matter that can be observed on visual inspection |
| | | | | | 30° C./65% RH | 1 M | 95.6 | 0.50 | 0.9 | | The solution is essentially free from particles of foreign matter that can be observed on visual inspection |
| Vancomycin HCl + LYSINE + NADA | 0.5% | 1.8% PEG 400 + 98.2% 0.9% NaCl | 1:20:30 | 4.9 | START | START | 96.2 | 0.56 | 0.3 | Renolit PE IV bags | The solution is essentially free from particles of foreign matter that can be observed on visual inspection |
| | | | | | 5° C. | 1 M | 96.1 | 0.53 | 0.3 | | The solution is essentially free from particles of foreign matter that can be observed on visual inspection |
| | | | | | 25° C./60% RH | 1 M | 95.8 | 0.52 | 0.6 | | The solution is essentially free from particles of foreign matter that can be observed on visual inspection |
| | | | | | 30° C./65% RH | 1 M | 95.1 | 0.53 | 0.9 | | The solution is essentially free from particles of foreign matter that can be observed on visual inspection |
| Vancomycin HCl + LYSINE + NADA | 0.5% | 1.8% PEG 400 + 98.2% 0.9% NaCl | 1:20:30 | 5.0 | START | START | 96.3 | 0.52 | 0.3 | Polycine PP IV bags | The solution is essentially free from particles of foreign matter that can be observed on visual inspection |
| | | | | | 5° C. | 1 M | NA | NA | NA | | The solution is essentially free from particles of foreign matter that can be observed on visual inspection |
| | | | | | 25° C./60% RH | 1 M | 95.9 | 0.55 | 0.5 | | The solution is essentially free from particles of foreign matter that can be observed on visual inspection |
| | | | | | 30° C./65% RH | 1 M | 95.6 | 0.54 | 0.9 | | The solution is essentially free from particles of foreign matter that can be observed on visual inspection |

The invention claimed is:

1. A liquid pharmaceutical composition comprising Vancomycin and sulfobutylether-betacyclodextrin, where the concentration of Vancomycin in the formulation is about from 0.5% to 10% w/V, wherein the pharmaceutical composition is stable for at least about four weeks at 25° C. in a closed container.

2. The pharmaceutical composition of claim 1, having a pH of about 2.0 to about 6.0.

3. The pharmaceutical composition of claim wherein the concentration of the Vancomycin is about 0.5 w/V, 5% w/V or 10% w/V.

4. The pharmaceutical composition of claim 1, wherein the Vancomycin and sulfobutylether-betacyclodextrin are present in a molar ratio of about 1:0.5 to 1:40 of Vancomycin:sulfobutylether-betacyclodextrin.

5. The pharmaceutical composition of claim 1, further comprising an organic solvent.

6. The pharmaceutical composition of claim 5, wherein the organic solvent comprises ethanol, propylene glycol or polyethylene glycol, or a combination thereof.

7. The pharmaceutical composition of claim 1, further comprising an amino acid.

8. The pharmaceutical composition of claim 7, wherein the amino acid is selected from D-Alanine, D-Serine, D-Leucine, D-Valine, L-Lysine, D-Lysine, L-Ornithine, D-Ornithine, and L-Arginine.

9. The pharmaceutical composition of claim 1, wherein the pharmaceutical composition is prepared for parenteral administration.

10. A method for stabilizing Vancomycin in a liquid pharmaceutical solution comprising mixing sulfobutylether-betacyclodextrin and Vancomycin in a ratio of Vancomycin to sulfobutylether-betacyclodextrin at which the pharmaceutical solution is stable for at least about four weeks at 25 degrees Celsius in a closed container, and where the concentration of Vancomycin in the solution is about from 0.5% to 10% w/V.

* * * * *

UNITED STATES PATENT AND TRADEMARK OFFICE
CERTIFICATE OF CORRECTION

PATENT NO. : 10,729,708 B2  
APPLICATION NO. : 16/300137  
DATED : August 4, 2020  
INVENTOR(S) : Sabina Keser et al.

Page 1 of 1

It is certified that error appears in the above-identified patent and that said Letters Patent is hereby corrected as shown below:

In the Claims

In Claim 3, Column 58, Line 58, "The pharmaceutical composition of claim wherein the" should read --The pharmaceutical composition of claim 1, wherein the--

Signed and Sealed this  
Seventeenth Day of November, 2020

Andrei Iancu  
*Director of the United States Patent and Trademark Office*